(12) United States Patent
Morishige et al.

(10) Patent No.: US 8,679,800 B2
(45) Date of Patent: Mar. 25, 2014

(54) METHOD FOR PRODUCING LACTIC ACID FROM PLANT-DERIVED RAW MATERIAL, AND LACTIC-ACID-PRODUCING BACTERIUM

(75) Inventors: Takashi Morishige, Mobara (JP); Katsuyuki Takahashi, Singapore (SG); Hitoshi Takahashi, Chiba (JP); Mitsufumi Wada, Chiba (JP); Daisuke Mochizuki, Mobara (JP); Daisuke Miyazawa, Mobara (JP); Tadashi Araki, Chiba (JP)

(73) Assignee: Mitsui Chemicals, Inc., Tokyo (JP)

( * ) Notice: Subject to any disclaimer, the term of this patent is extended or adjusted under 35 U.S.C. 154(b) by 174 days.

(21) Appl. No.: 13/063,929

(22) PCT Filed: Sep. 11, 2009

(86) PCT No.: PCT/JP2009/065957
§ 371 (c)(1),
(2), (4) Date: Mar. 14, 2011

(87) PCT Pub. No.: WO2010/032698
PCT Pub. Date: Mar. 25, 2010

(65) Prior Publication Data
US 2011/0171704 A1    Jul. 14, 2011

(30) Foreign Application Priority Data

Sep. 16, 2008  (JP) ................ 2008-237177
Feb. 13, 2009  (JP) ................ 2009-032043

(51) Int. Cl.
| | | |
|---|---|---|
| C12P 7/56 | (2006.01) |
| C12N 9/00 | (2006.01) |
| C12N 1/20 | (2006.01) |
| C12N 15/00 | (2006.01) |
| C07H 21/04 | (2006.01) |

(52) U.S. Cl.
USPC ..... 435/139; 435/183; 435/252.3; 435/320.1; 536/23.2

(58) Field of Classification Search
None
See application file for complete search history.

(56) References Cited

U.S. PATENT DOCUMENTS

| 6,960,455 B2 | 11/2005 | Livshits et al. |
| 2007/0065930 A1 | 3/2007 | Wada et al. |
| 2010/0203602 A1 | 8/2010 | Zhou et al. |

FOREIGN PATENT DOCUMENTS

| CN | 1856577 A | 11/2006 |
| EP | 1 669 460 | 6/2006 |
| JP | 2001-346578 | 12/2001 |
| JP | 2007-049993 | 3/2007 |
| WO | WO-2005/033324 A1 | 4/2005 |
| WO | WO-2009/078687 A2 | 6/2009 |

OTHER PUBLICATIONS

International Search Report in PCT/JP2009/065957 dated Oct. 13, 2009.
Jahreis, et al. "Adadaption of Sucrose Metabolism in the *Escherichia coli* Wild-Type Strain EC3132†", Journal of Bacteriology, Oct. 2002, vol. 184, No. 19, pp. 5307-5316.
Mochizuki, et al. "D-nyusan o Sentakuteki ni Koseisan suru Daichokin no Ikushu", Abstracts of the Annual Meeting of the Society for Biotechnology, Japan, Aug. 25, 2004, p. 253, 2K16-3.
Orchard, et al. "Sequence similarities between the gene specifying 1-phosphofructokinase (*fruK*), genes specifying other kinases in *Escherichia coli* K12, and *lacC* of *Staphylococcus aureus*", Proc Biol Sci, 1990, vol. 242, pp. 87-90.
Sahin-Toth, et al. "Cloning, sequencing, and expression of *cscA* invertase from *Escherichia coli* B-62", Can. J. Microbiol, 1999, vol. 45, pp. 418-422.
Shukla, et al. "Production of D(-)-lactate from sucrose and molasses" Biotechnolgy Letters, 2004, vol. 26, pp. 689-693.
Sproul, et al. "Genetic control of manno(fructo)kinase activity in *Escherichia coli*", PNAS, Dec. 18, 2001, vol. 98, No. 26, pp. 15257-15259.
Voronovsky, et al. "Expression of *xyl A* genes encoding xylose isomerases from *Escherichia coli* and *Streptomyces coelicolor* in the methylotrophic yeast *Hansenula polymorpha*" FEMS Yeast Research, 2005, vol. 5, pp. 1055-1062.
Zhou, et al. "Fermentation of 10% (w/v) sugar to D(-)-lactate by engineered *Escherichia coli* B", Biotechnology Letters, 2005, vol. 27, pp. 1891-1896.
Office Action Chinese Application No. 200980135975.2, dated Aug. 28, 2012.
Dien et al., "Recombinant *Escherichia coli* engineered for production of L-lactic acid from hexose and pentose sugars", Journal of Industrial Microbiology and Biotechnology, Basingstoke, GB, vol. 27, No. 4, pp. 259-264, Oct. 1, 2001, XP002419005.
European Search Report dated Nov. 15, 2012 issued in connection with European Application No. 09814542.8.
Boris Görke et al., "Carbon catabolite repression in bacteria: many ways to make the most out of nutrients", Nature Reviews | Microbiology, vol. 6, Aug. 2008, pp. 613-624.
Dan G. Fraenkel, "Glycolysis—14", *Escherichia coli* and *Salmonella*, Cellular and Molecular Biology, Second Edition, Frederick C. Nedhardi, Editor in Chief, 1996 ASM Press, 2 pgs.

(Continued)

*Primary Examiner* — Christian Fronda
(74) *Attorney, Agent, or Firm* — Foley & Lardner LLP

(57) ABSTRACT

The present invention provides: a lactic acid-producing *Escherichia coli* comprising at least one gene of a sucrose non-PTS gene group, including at least a sucrose hydrolase gene, provided that a combination of a repressor protein (cscR), a sucrose hydrolase (cscA), a fructokinase (cscK) and a sucrose permease (cscB) and a combination of a sucrose hydrolase (cscA), a fructokinase (cscK) and a sucrose permease (cscB) are excluded, wherein the lactic acid-producing *Escherichia coli* comprises a lactic acid production enhancing system provided by genetic recombination; and a lactic acid production method including producing lactic acid from a plant-derived sucrose-containing raw material by using the lactic acid-producing *Escherichia coli*.

12 Claims, 1 Drawing Sheet

(56) References Cited

OTHER PUBLICATIONS

Jacqueline Plumbridge, "Regulation of gene expression in the PTS in *Escherichia coli*: the role and interactions of Mlc", Current Opinion in Microbiology 2002, 5:187-193.

F. Daldal et al., "Tn10 insertions in the pfkB region of *Escherichia coli*.", J. Bacteriol. 1981, 147(3): 935-938.

Alan Berry et al., "Identification of zinc-binding ligands in the Class II fructose-1,6-bisphosphate aldolase of *Escherichia coli*", FEBS 12115, vol. 318, No. 1, Feb. 1993, pp. 11-16.

Graeme J. Thomson et al., "The *dhnA* gene of *Eschericia coli* encodes a Class I fructose bisphosphate aldolase", Biochem. J. (1998) 331, 437-445.

Heather I. Fraser et al., "The two analogous phosphoglycerate mutases of *Escherichia coli*", FEBS Letters 455 (1999), 344-348.

E. Ponce et al., "Cloning of the two pyruvate kinase isoenzyme structural genes from *Escherichia coli*: the relative roles of these enzymes in pyruvate biosynthesis", Journal of Bacteriology 1995, 177(19):5719-5722.

G. Zhao et al., "An *Escherichia coli* K-12 tktA tktB mutant deficient in transketolase activity requires pyridoxine (vitamin B6) as well as the aromatic amino acids and vitamins for growth", J. Bacteriol. 1994, 176(19):6134-6138.

K.I. Sørensen et al., "Ribose catabolism of *Escherichia coli*: characterization of the rpiB gene encoding ribose phosphate isomerase B and the rpiR gene, which is involved in regulation of rpiB expression", Journal of Bacteriology, 1996, 178(4):1003-1011.

Non-Final Office Action U.S. Appl. No. 13/063,923 dated Apr. 9, 2013.

Non-Final Office Action U.S. Appl. No. 13/063,923 dated Feb. 6, 2013.

Written Opinion PCT/JP2009/065956 (English Translation) filed Apr. 18, 2011.

Notice of Allowance issued for U.S. Appl. No. 13/063,923 dated Aug. 19, 2013.

Extended European Search Report dated Jan. 3, 2014 received in European Application No. 09814543.

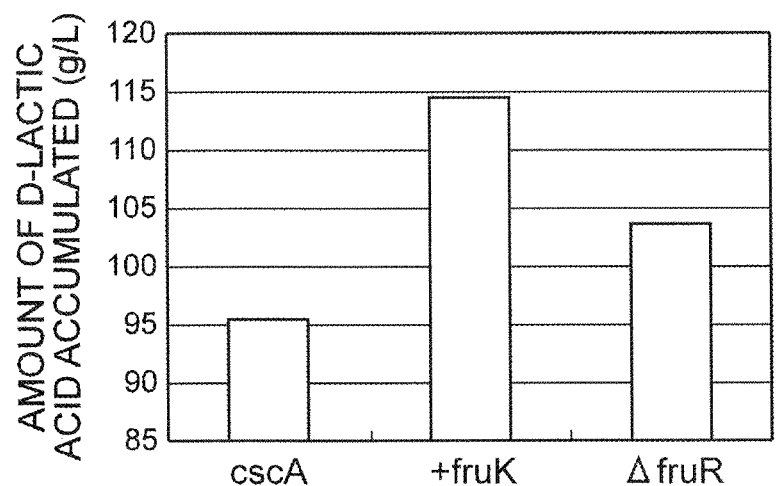

METHOD FOR PRODUCING LACTIC ACID FROM PLANT-DERIVED RAW MATERIAL, AND LACTIC-ACID-PRODUCING BACTERIUM

TECHNICAL FIELD

The present invention relates to a method of producing lactic acid from a plant-derived raw material and a lactic acid-producing bacterium.

RELATED ART

Lactic acid is a useful substance, to which attention has been paid in recent years as a raw material for polymers or an intermediate for agrochemicals and medicines. Lactic acid includes L-lactic acid and D-lactic acid. Polylactic acid that is industrially produced at present is an L-lactic acid polymer. However, D-lactic acid has also attracted increasing attention in recent years as a raw material for polymers or an intermediate for agrochemicals and medicines. In nature, microorganisms that produce lactic acid with high efficiency, such as *Lactobacillus* and filamentous bacteria, are present. Known methods for producing lactic acid using the microorganisms include a method using *Lactbacillus delbrueckii* or the like as a microorganism producing L-lactic acid with high efficiency, and a method using microorganisms belonging to genus *Sporolactobacillus* or the like as microorganisms producing D-lactic acid with high efficiency.

However, lactic acid as a raw material is required to have high optical purity in either use.

With recent advancement of research, microorganisms that produce D-lactic acid with high selectivity and high productivity have been invented (see Pamphlet of International Publication (WO) No. 2005/033324).

Further, there is also known an *Escherichia coli* that produces D-lactic acid with high productivity from sucrose, which is an inexpensive sugar raw material (see Biotechnology Letters, Vol. 27, pp. 1891-1896 (2005)). However, the *Escherichia coli* that produces D-lactic acid from sucrose has low productivity and takes a very long period of time to assimilate sucrose, which imposes a problem on industrialization.

With respect to L-lactic acid, an *Escherichia coli* that produces L-lactic acid with high selectivity and high productivity using glucose as a raw material is known (Japanese Patent Application Laid-Open (JP-A) No. 2007-49993). However, an *Escherichia coli* that produces L-lactic acid from sucrose is not known.

Based on conventional understanding, the mechanisms of sucrose assimilation by a microorganism are roughly divided into a sucrose PTS (Phosphoenolpyruvate:Carbohydrate Phosphotransferase System) and a sucrose non-PTS (for example, JP-A No. 2001-346578). When the sucrose assimilation takes place via the sucrose non-PTS, the microorganism incorporates sucrose as it is, and then decomposes the sucrose into glucose and fructose. On the other hand, when the sucrose assimilation takes place via the sucrose PTS, the microorganism phosphorylates sucrose when incorporating the sucrose, and then converts the sucrose into sucrose-6-phosphate. Thereafter, the sucrose-6-phosphate is decomposed into glucose-6-phosphate and fructose inside the microorganism.

That is, in either mechanism, sucrose-derived fructose appears inside a microorganism in a non-phosphorylated form at first. In order to incorporate the fructose that is not phosphorylated (hereinafter referred to as "non-phosphorylated fructose") into a glycolytic system, the fructose needs to be isomerized into glucose or phosphorylated. However, literature suggests that an activity of isomerizing non-phosphorylated fructose into glucose and an activity of phosphorylating fructose are both very low in a case in which the microorganism is an *Escherichia coli* (except for some *Escherichia coli* strains that are capable of assimilating sucrose) (see FEMS Yeast Res., Vol. 5, pp. 1055-1062 (2005); PNAS, Vol. 98(26), pp. 15257-15259 (2001); and J. Bacteriology, Vol. 184(19), pp. 5307-5316 (2002)). Therefore, even if non-phosphorylated fructose were successfully made to appear inside an *Escherichia coli*, assimilation of the non-phosphorylated fructose by the *Escherichia coli* would not be expected unless special measures were taken.

It is known that the sucrose non-PTS is composed of four factors, CscB (which incorporates sucrose), CscA (which decomposes sucrose inside microorganisms), CscK (which phosphorylates fructose), and CscR (which controls the expression of CscB, A, and K). Biotechnology Letters, Vol. 27, pp. 1891-1896 (2005) describes that introduction of the four factors into a D-lactic acid-producing *Escherichia coli* achieved production from sucrose at a yield of 93% relative to sugar, and a productivity of 96.5 g/L/120 hours. However, the productivity is at an insufficient level in terms of industrialization, and a further improvement in productivity is required.

Further, Can. J. Microbiol., Vol. 45, pp. 418-422 (1999) discloses that an *Escherichia coli* became to be able to grow on sucrose as a raw material by introduction of cscA alone into the *Escherichia coli*. However, this document does not describe assimilation of sucrose-derived fructose. One important issue in the production of a substance by an *Escherichia coli* using sucrose as a raw material is achievement of high yield production from the sucrose raw material. Efficient assimilation of sucrose-derived fructose as well as sucrose-derived glucose is an essential condition for the achievement of high yield. Whilst this document demonstrates that the introduction of CscA alone into an *Escherichia coli* resulted in assimilation of sucrose, this document does not disclose any data as to the degree of the assimilation of sucrose-derived fructose.

With regard to cscA, it is known that the production of amino acids derived from phosphoenolpyruvic acid (PEP), for example tryptophan, is further improved by the introduction of cscA, cscB, cscK and cscR genes (for example, JP-A No. 2007-49993).

As described above, conventional methods for lactic acid production from sucrose still have low productivity and take a very long time to assimilate sucrose. Therefore, there is still a need for improvement in technologies for industrial production of lactic acid sufficiently utilizing sucrose, which is inexpensive and has high industrial utility value.

SUMMARY OF INVENTION

Technical Problem

It is an object of the present invention to provide a lactic acid-producing bacterium that assimilates sucrose in a shorter time and that is useful for production of lactic acid from sucrose at higher efficiency, and a method of producing lactic acid.

Technical Solution

The present invention provides a lactic acid-producing bacterium and a method of producing lactic acid. That is, the present invention includes the following.

[1]. A lactic acid-producing *Escherichia coli* comprising at least one gene of a sucrose non-PTS gene group, including at least a sucrose hydrolase gene, provided that a combination of a repressor protein (cscR), a sucrose hydrolase (cscA), a fructokinase (cscK) and a sucrose permease (cscB) and a combination of a sucrose hydrolase (cscA), a fructokinase (cscK) and a sucrose permease (cscB) are excluded,
wherein the lactic acid-producing *Escherichia coli* comprises a lactic acid production enhancing system provided by genetic recombination.

[2]. The lactic acid-producing *Escherichia coli* as described in [1], wherein the lactic acid-producing *Escherichia coli* comprises only the sucrose hydrolase gene from among the sucrose non-PTS gene group, and the lactic acid-producing *Escherichia coli* comprises the lactic acid production enhancing system provided by genetic recombination.

[3]. The lactic acid-producing *Escherichia coli* as described in [1] or [2], wherein the lactic acid-producing *Escherichia coli* further comprises a fructose metabolism ability improvement system.

[4]. The lactic acid-producing *Escherichia coli* as described in any one of [1] to [3], wherein the lactic acid production enhancing system includes inactivation or attenuation of pyruvate-formate lyase activity.

[5]. The lactic acid-producing *Escherichia coli* as described in any one of [1] to [4], wherein the lactic acid production enhancing system includes enhancement of NADH-dependent lactate dehydrogenase activity for producing D-lactic acid or L-lactic acid.

[6]. The lactic acid-producing *Escherichia coli* as described in any one of [1] to [4], wherein the lactic acid production enhancing system includes enhancement of D-lactate dehydrogenase activity and inactivation or attenuation of innate FAD-dependent D-lactate dehydrogenase activity of the *Escherichia coli*.

[7]. The lactic acid-producing *Escherichia coli* as described in any one of [1] to [4], wherein the lactic acid production enhancing system includes enhancement of L-lactate dehydrogenase activity and inactivation or attenuation of at least one of innate D-lactate dehydrogenase activity of the *Escherichia coli* or innate FMN-dependent L-lactate dehydrogenase activity of the *Escherichia coli*.

[8]. The lactic acid-producing *Escherichia coli* as described in any one of [3] to [7], wherein the fructose metabolism ability improvement system is enhancement of phosphorylation ability or enhancement of fructose uptake ability in a fructose metabolism pathway.

[9]. The lactic acid-producing *Escherichia coli* as described in [8], wherein the enhancement of phosphorylation ability in a fructose metabolism pathway is derived from fructose-1-phosphate kinase activity.

[10]. The lactic acid-producing *Escherichia coli* as described in [8], wherein the enhancement of fructose uptake ability in a fructose metabolism pathway is derived from inactivation or attenuation of innate FruR activity of the *Escherichia coli*.

[11]. The lactic acid-producing *Escherichia coli* as described in any one of [1] to [10], wherein the sucrose hydrolase gene is derived from a bacterium belonging to the genus *Escherichia*.

[12]. The lactic acid-producing *Escherichia coli* as described in any one of [1] to [10], wherein the sucrose hydrolase gene is derived from an *Escherichia coli* O157 bacterium.

[13]. The lactic acid-producing *Escherichia coli* as described in any one of [9] to [12], wherein the fructose-1-phosphate kinase is derived from a bacterium belonging to the genus *Escherichia*.

[14]. The lactic acid-producing *Escherichia coli* as described in any one of [9] to [12], wherein the fructose-1-phosphate kinase is a protein derived from *Escherichia coli* MG1655.

[15]. The lactic acid-producing *Escherichia coli* as described in any one of [1] to [14], wherein the lactic acid-producing *Escherichia coli* is a variant derived from *Escherichia coli* K12.

[16]. A method for producing lactic acid, the method comprising:
producing lactic acid from a plant-derived sucrose-containing raw material by using the lactic acid-producing *Escherichia coli* described in any one of [1] to [15].

Advantageous Effects of Invention

According to the invention, a lactic acid-producing bacterium that assimilates sucrose in a shorter time and that is useful for lactic acid production at higher efficiency, and a method of producing lactic acid, are provided.

BRIEF DESCRIPTION OF DRAWINGS

FIG. 1 is a graph showing the accumulation amount of produced lactic acid when 48-hour culture has conducted using various lactic acid-producing bacteria according to Example 10 of the invention.

EMBODIMENTS FOR CARRYING OUT INVENTION

The lactic acid-producing bacterium according to the invention is a lactic acid-producing *Escherichia coli* that has at least one gene of a sucrose non-PTS gene group, including at least a sucrose hydrolase gene (provided that a combination of a repressor protein (cscR), a sucrose hydrolase (cscA), a fructokinase (cscK), and a sucrose permease (cscB), and a combination of a sucrose hydrolase (cscA), a fructokinase (cscK), and a sucrose permease (cscB), are excluded), wherein the lactic acid-producing *Escherichia coli* has a lactic acid production enhancing system provided by genetic recombination.

The method of producing lactic acid according to the invention is a method of producing lactic acid including producing lactic acid from a plant-derived sucrose-containing raw material by using the lactic acid-producing bacterium.

The lactic acid-producing bacterium according to the invention has at least one gene, including at least a sucrose hydrolase gene, of the sucrose non-PTS gene group (provided that a combination of a repressor protein (cscR), a sucrose hydrolase (cscA), a fructokinase (cscK), and a sucrose permease (cscB), and a combination of a sucrose hydrolase (cscA), a fructokinase (cscK), and a sucrose permease (cscB), are excluded) and also has a lactic acid production enhancing system, as a result of which the lactic acid-producing bacterium according to the invention can phosphorylate sucrose-derived fructose, incorporate the sucrose-derived fructose into the cell, and convert the fructose into lactic acid using the lactic acid production enhancing system. Hitherto, there has been no report on any example in which at least one gene of the sucrose non-PTS gene group, including at least a sucrose hydrolase gene, is imparted to a bacterium that does not have sucrose assimilation ability so as to produce a substance by using sucrose as a carbon source.

In the invention, it has been found that sucrose-derived fructose is assimilated with high efficiency and the productivity is noticeably increased as compared to conventional methods, when some, but not all, of the genes of the sucrose non-PTS gene group are introduced are introduced into a lactic acid-producing *Escherichia coli*, i.e., when at least one sucrose non-PTS gene, including at least a sucrose hydrolase gene, into a lactic acid-producing *Escherichia coli*. As a consequence, lactic acid can be obtained in a short time from plant-derived sucrose, which is inexpensive and has high industrial value.

In particular, the lactic acid-producing bacterium according to the invention is able to produce lactic acid by assimilation of sucrose, or fructose, which is a decomposition product of sucrose, irrespective of whether glucose as another sugar source is present or absent. Therefore, the lactic acid-producing bacterium according to the invention is more efficient since the lactic acid-producing bacterium is able to produce lactic acid even before other sugar substrates such as glucose have decreased or depleted.

It is known that, generally, that uptake of glucose is usually preferred to fructose uptake in *Escherichia coli*, and thus fructose is not sufficiently metabolized in the presence of glucose. Further, sugar metabolism is a fundamental function of organisms. Therefore, it is surprising that the enhancement of phosphorylation activity or fructose uptake ability of the fructose metabolism pathway achieved efficient production of lactic acid without causing suppression of bacterial growth and without being influenced by catabolite repression by glucose.

The term "sucrose non-PTS gene group" as used in the invention refers to a group of genes involved in the non-PTS system of the sucrose assimilation pathway of a microorganism. Specifically, the sucrose non-PTS gene group is a gene group consisting of a repressor protein (cscR), a sucrose hydrolase (cscA), a fructokinase (cscK), and a sucrose permease (cscB). In the invention, at least one gene that includes at least a cscA and that is selected from these genes is used, and examples the at least one gene include a cscA alone, a combination of a cscA and a cscK, a combination of a cscA and a cscB, a combination of a cscA and a cscR, a combination of a cscA, a cscB, and a cscR, and a combination of a cscA, a cscK, and a cscR. In the invention, a combination of a repressor protein (cscR), a sucrose hydrolase (cscA), a fructokinase (cscK), and a sucrose permease (cscB), and a combination of a sucrose hydrolase (cscA), a fructokinase (cscK), and a sucrose permease (cscB) are excluded from possible combinations of genes of the sucrose non-PTS gene group to be introduced.

In particular, it is preferable that the at least one gene to be introduced includes only the gene encoding cscA, and does not include other genes, from the viewpoint of more efficiently producing lactic acid.

The term "sucrose hydrolase (invertase, CscA)" as used in the invention is a generic term for enzymes that are classified to enzyme number 3.2.1.26 according to the enzyme committee report of the International Union of Biochemistry (I.U.B.), and that catalyze a reaction of generating D-glucose and D-fructose from sucrose.

This enzyme is an enzyme that *Escherichia coli* of K12 strain or the like does not naturally possess, and this enzyme is one of the enzymes of the non-PTS metabolism pathway including a proton co-transporter, an invertase, a fructokinase, and a sucrose-specific repressor (see Canadian Journal of Microbiology, (1991) vol. 45, pp 418-422). As a result of the impartment of CscA in the invention (especially the impartment of cscA alone), sucrose outside the bacterial cell is decomposed into glucose and fructose on the cell membrane and released to outside the cell, and they are phosphorylated and incorporated into the cytoplasm via a glucose PTS and a fructose PTS. As a result, fructose can be supplied to a fructose metabolism system of the bacterium, and can be assimilated using a glycolytic system.

As the gene of the sucrose hydrolase (invertase, CscA) to be introduced into the host bacterium according to the invention, a DNA having the base sequence of a gene that encodes a sucrose hydrolase (invertase, CscA) and that is obtained from an organism having the enzyme, or a synthetic DNA sequence synthesized based on a known base sequence of the gene, may be used. Preferable examples thereof include those derived from bacteria belonging to the genus *Erwinia*, bacteria belonging to the genus *Proteus*, bacteria belonging to the genus *Vibrio*, bacteria belonging to the genus *Agrobacterium*, bacteria belonging to the genus *Rhizobium*, bacteria belonging to the genus *Staphylococcus*, bacteria belonging to the genus *Bifidobacterium*, and bacteria belonging to the genus *Escherichia*. Examples thereof include a DNA having the base sequence of a gene derived from an *Escherichia coli* O157 strain. A DNA having the base sequence of a gene derived from an *Escherichia coli* O157 strain is particularly preferable. Further, it is preferable that a signal sequence for transferring the cscA to the periplasm of the bacterial cell is added to the cscA.

As the gene of the repressor protein (CscR) to be introduced into the host bacterium according to the invention, a DNA having the base sequence of a gene that encodes a repressor protein (CscR) and that is obtained from an organism having the enzyme, or a synthetic DNA sequence synthesized based on a known base sequence of the gene, may be used. Preferable examples thereof include those derived from bacteria belonging to the genus *Erwinia*, bacteria belonging to the genus *Proteus*, bacteria belonging to the genus *Vibrio*, bacteria belonging to the genus *Agrobacterium*, bacteria belonging to the genus *Rhizobium*, bacteria belonging to the genus *Staphylococcus*, bacteria belonging to the genus *Bifidobacterium*, and bacteria belonging to the genus *Escherichia*. Examples thereof include a DNA having the base sequence of a gene derived from an *Escherichia coli* O157 strain. A DNA having the base sequence of a gene derived from an *Escherichia coli* O157 strain is particularly preferable.

As the gene of the fructokinase (CscK) to be introduced into the host bacterium according to the invention, a DNA having the base sequence of a gene that encodes a fructokinase (CscK) and that is obtained from an organism having the enzyme, or a synthetic DNA sequence synthesized based on a known base sequence of the gene, may be used. Preferable examples thereof include those derived from bacteria belonging to the genus *Erwinia*, bacteria belonging to the genus *Proteus*, bacteria belonging to the genus *Vibrio*, bacteria belonging to the genus *Agrobacterium*, bacteria belonging to the genus *Rhizobium*, bacteria belonging to the genus *Staphylococcus*, bacteria belonging to the genus *Bifidobacterium*, and bacteria belonging to the genus *Escherichia*. Examples thereof include a DNA having the base sequence of a gene derived from an *Escherichia coli* O157 strain. A DNA having the base sequence of a gene derived from an *Escherichia coli* O157 strain is particularly preferable.

As the gene of the sucrose permease (CscB) to be introduced into the host bacterium according to the invention, a DNA having the base sequence of a gene that encodes a sucrose permease (CscB) and that is obtained from an organism having the enzyme, or a synthetic DNA sequence synthesized based on a known base sequence of the gene, may be used. Preferable examples thereof include those derived from bacteria belonging to the genus *Erwinia*, bacteria belonging to the genus *Proteus*, bacteria belonging to the genus *Vibrio*, bacteria belonging to the genus *Agrobacterium*, bacteria belonging to the genus *Rhizobium*, bacteria belonging to the genus *Staphylococcus*, bacteria belonging to the genus *Bifidobacterium*, and bacteria belonging to the genus *Escherichia*. Examples thereof include a DNA having the base sequence of a gene derived from an *Escherichia coli* O157 strain. A DNA having the base sequence of a gene derived from an *Escherichia coli* O157 strain is particularly preferable.

The term "sucrose assimilation" as used in the invention refers to ability that incorporates sucrose directly or after converting it to substances having lower molecular weights or after converting it to a substance having a higher molecular weight (among which conversion to substances having lower molecular weights is preferable), or ability that metabolically converts sucrose to another substance. Further, the term "assimilation" as used in the invention includes decomposition that further converts sucrose into a substance having lower molecular weights. Specifically, assimilation includes decomposition of sucrose into D-glucose and D-fructose.

The term "fructose metabolism ability improvement" as used in the invention refers to a state in which incorporation of fructose into the bacterial cell is increased. The fructose metabolism ability improvement system means a structure for improving the fructose metabolism ability.

Further, the term "host" as used in the invention means an *Escherichia coli* that becomes the lactic acid-producing *Escherichia coli* according to the invention as a result of introduction of one or more genes from outside the bacterial cell.

Each numerical range described in the present specification represents a range including the indicated values as the minimum value and the maximum value, respectively.

The term "lactic acid production enhancing system" in the invention refers to a structure for improving lactic acid-producing ability wherein the structure is introduced or altered by genetic recombination. The lactic acid production enhancing system may be any system as long as it increases lactic acid production in a target *Escherichia coli* compared to original lactic acid production. Preferable examples of the system include inactivation, attenuation or enhancement of enzymatic activity involved in lactic acid-producing activity, and a combination thereof. This system, when combined with the CscA activity, enables an *Escherichia coli* that originally lacked sucrose assimilation ability to effectively produce lactic acid from sucrose.

The expression "by genetic recombination" as used in the invention encompasses any change in the base sequence due to insertion of a different DNA into the base sequence of an innate gene, or a substitution or deletion of a certain portion of a gene, or a combination thereof. For example, the change may be a result of mutation.

The term "inactivation" as used in the invention refers to a state in which the activity of the enzyme of interest or transcription factor FruR measured is below the detection limit regardless of the measurement system from among existing measurement systems. The "activity of FruR" as used herein refers to a quantified value of the amount or function of proteins generated by the expression of genes that are controlled by FruR.

The "attenuation" in the invention refers to a state in which the activity of the enzyme of interest or transcription factor FruR is significantly decreased by genetic recombination of the gene encoding the enzyme or FruR, as compared to a state before the recombination treatment is conducted. The "activity of FruR" as used herein refers to a quantified value of the amount or function of proteins generated by the expression of genes that are controlled by FruR.

The lactic acid production enhancing system according to the invention preferably includes inactivation or attenuation of activity of pyruvate-formate lyase (Pfl), enhancement of NADH-dependent lactate dehydrogenase activity for producing D-lactic acid or L-lactic acid, or both, from the viewpoint of reducing by-products and increasing the yield of lactic acid (regarding the inactivation or attenuation of pyruvate-formate lyase (Pfl) activity, see WO2005/033324; regarding the enhancement of NADH-dependent D-lactate dehydrogenase activity, see a document by Yang, et al (Metab. Eng. Vol. 1(2), pp 141-152 (1999)).

The pyruvate-formate lyase (Pfl) in the invention is an enzyme that is classified to enzyme number 2.3.1.54 according to the enzyme committee report of the International Union of Biochemistry (I.U.B.), and is also called formate acetyl transferase. The "pyruvate-formate lyase" is a generic name for enzymes that reversibly catalyze a reaction of generating formic acid from pyruvic acid.

Examples of the NADH-dependent lactate dehydrogenase in the invention include D-lactate dehydrogenase (LdhA) and L-lactate dehydrogenase (Ldh2). LdhA refers to an *Escherichia coli*-derived enzyme that generates D-lactic acid and NAD from pyruvic acid and NADH. Ldh2 refers to an enzyme that generates L-lactic acid and NAD from pyruvic acid and NADH, and examples thereof include an enzyme derived from *Bifidobacterium longum*.

The expression "enhancement of lactate dehydrogenase activity" as used in the invention refers to a state in which the activity of the enzyme produced from a gene encoding LdhA or Ldh2 is significantly increased by genetic recombination of the gene encoding LdhA or Ldh2, as compared to the state before the recombination treatment is conducted.

Lactic acid includes optical isomers of D-lactic acid and L-lactic acid. In the invention, a system that includes enhancement of NADH-dependent D-lactate dehydrogenase activity or NADH-dependent L-lactate dehydrogenase in order to increase the yield of either optical isomer, is specially referred to as "system for D-lactic acid production enhancement" or "system for L-lactic acid production enhancement" in some cases. Therefore, the kind of lactic acid production enhancing system may be selected, as appropriate, depending on the desired kind of lactic acid.

Particularly, the system for D-lactic acid production enhancement may further include inactivation or attenuation of innate FAD-dependent D-lactate dehydrogenase (Dld) activity of the *Escherichia coli* in order to generate D-lactic acid more rapidly. The system for D-lactic acid production enhancement more preferably includes both (i) inactivation or attenuation of innate FAD-dependent D-lactate dehydrogenase (Dld) activity of the *Escherichia coli* and (ii) at least one of (a) inactivation or attenuation of pyruvate-formate lyase (Pfl) activity or (b) enhancement of NADH-dependent D-lactate dehydrogenase activity, and most preferably includes inactivation or attenuation of Dld activity and both (i) inactivation or attenuation of Pfl activity and (ii) enhancement of *Escherichia coli*-derived NADH-dependent D-lactate dehydrogenase (LdhA) activity.

Further, the system for L-lactic acid production enhancement may further include inactivation or attenuation of innate FMN-dependent L-lactate dehydrogenase (LldD) activity or innate D-lactate dehydrogenase (LdhA) activity of the

*Escherichia coli*, preferably simultaneous inactivation or attenuation of LldD activity and LdhA activity, in order to generate L-lactic acid more rapidly. It is more preferable that at least one activity of pfl activity, lld activity, or ldhA activity is inactivated or attenuated while NADH-dependent L-lactate dehydrogenase activity is enhanced. It is most preferable that Pfl activity and both of LldD activity and LdhA activity are inactivated or attenuated while *Bifidobacterium*-derived NADH-dependent L-lactate dehydrogenase activity is enhanced.

The FMN-dependent L-lactate dehydrogenase (LldD) in the invention is an enzyme classified to enzyme number 1.1.2.3 according to the enzyme committee report of the International Union of Biochemistry (I.U.B.). The "FMN-dependent L-lactate dehydrogenase" is a generic name for enzymes that catalyze a reaction of generating pyruvic acid from L-lactic acid.

An example of the bacterium in which LdhA activity is enhanced and Pfl activity is inactivated or attenuated in the invention is MT-10934/pGlyldhA described in WO2005/033324.

A method including integrating a gene encoding LdhA or Ldh2 into an expression plasmid so as to be linked to a gene promoter that controls expression of a protein involved in a glycolytic system, a nucleic acid biosynthesis system, or an amino acid biosynthesis system, and introducing the expression plasmid into a desired bacterium, is an effective measure for enhancing LdhA activity or Ldh2 activity in the invention. In this case, the gene promoter that controls the expression of a protein involved in the glycolytic system, the nucleic acid biosynthesis system, or the amino acid biosynthesis system refers to a strong promoter that constantly functions in a bacterium, preferably in *Escherichia coli*, and that is less susceptible to expression suppression even in the presence of glucose. Specific examples thereof include the promoter of glyceraldehyde-3-phosphate dehydrogenase or the promoter of serine hydroxymethyltransferase (GlyA). The bacterium thus obtained exhibits an increased accumulation amount of D-lactic acid or L-lactic acid, a reduced concentration of pyruvic acid as an impurity, and can improve optical purity of D-lactic acid or L-lactic acid when producing D-lactic acid or L-lactic acid under aerobic conditions, as compared to a case in which ldhA or ldh2 expression is not enhanced.

The "FAD-dependent D-lactate dehydrogenase (Dld)" in the invention is a generic name for enzymes that catalyze a reaction of generating pyruvic acid from D-lactic acid in the presence of oxidized flavin adenine dinucleotide serving as a coenzyme.

An example of a microorganism in which Dld activity is inactivated or attenuated, and/or Pfl activity is inactivated or attenuated, and/or LdhA activity is enhanced in the invention may be an *Escherichia coli* MT-10994 (FERM BP-10058) strain described in WO2005/033324.

The gene promoter that controls the expression of a protein involved in the glycolytic system, the nucleic acid biosynthesis system, or the amino acid biosynthesis system in the invention refers to a strong promoter that constantly functions in a microorganism and that is less susceptible to expression suppression even in the presence of glucose. Specific examples thereof include the promoter of glyceraldehyde-3-phosphate dehydrogenase (hereinafter sometimes referred to as "GAPDH") or the promoter of serine hydroxymethyltransferase.

The promoter in the invention refers to a site to which RNA polymerase having a sigma factor binds and at which transcription is initiated. For example, the *Escherichia coli*-derived GAPDH promoter is described at Base Nos. 397 to 440 in the base sequence information of GenBank accession number X02662.

The microorganism in which a gene promoter that controls expression of a protein involved in the glycolytic system, the nucleic acid biosynthesis system, or the amino acid biosynthesis system allows a gene encoding LdhA on the genome to expresses the ldhA, Pfl activity is inactivated or attenuated, and/or Dld activity is inactivated or attenuated in the invention may be, for example, an *Escherichia coli* MT-10994 (FERM BP-10058) strain described in WO2005/033324.

The *Escherichia coli* MT-10994 strain is configured to express an ldhA gene due to functional linking of the ldhA gene to the GAPDH promoter on the genome, and PflB and Dld thereof are inactivated by gene disruption. This strain has been deposited since Mar. 19, 2004 with a deposition number FERM BP-10058 at International Patent Organism Depositary of National Institute of Advanced Industrial Science and Technology at Central 6, 1-1-1 Higashi, Tsukuba City, Ibaraki Prefecture, conforming with the Budapest Treaty on the International Recognition of the Deposit of Microorganisms for the Purposes of Patent Procedure.

It is preferable, from the viewpoint of lactic acid production efficiency, that the lactic acid-producing bacterium according to the invention further includes a fructose metabolism ability improvement system. Examples of the fructose metabolism ability improvement system include a system that enhances phosphorylation ability or fructose uptake ability in a fructose metabolism pathway. It is more preferable, from the viewpoint of lactic acid production efficiency, that the enhancement of phosphorylation ability in a fructose metabolism pathway is impartment of fructose-1-phosphate kinase activity, and the enhancement of fructose uptake ability is derived from attenuation of FruR activity.

The scope of the "impartment" or "enhancement" of ability in the invention encompasses introduction of an enzyme-encoding gene into a host bacterium from the outside of the bacterium to the inside of the bacterium, enhancement of the promoter activity for an enzyme gene that the host bacterium possesses on its genome, and strong expression of an enzyme gene caused by replacement with another promoter.

The "enhancement of phosphorylation ability" in the invention refers to a state in which the activity of a phosphorylation enzyme is increased so that the amount of a phosphorylated substrate or the amount of a metabolite derived from the phosphorylated substrate is significantly increased.

The "enhancement of fructose uptake ability" in the invention refers to a state in which the activity of enzymes controlled by FruR is significantly decreased by genetic recombination of a gene encoding FruR, as compared to a state before the recombination treatment is conducted.

The activity of an enzyme in the invention may be activity as measured by any of existing measurement systems.

The fructose-1-phosphate kinase (FruK) in the invention is an enzyme classified to enzyme number 2.7.1.56 according to the enzyme committee report of the International Union of Biochemistry (I.U.B.), and is also referred to as "phosphofructokinase 1". Uptake of fructose by bacteria, such as *Escherichia coli*, is generally suppressed in the presence of glucose. Heretofore, there has been no finding that enhanced expression of FruK promotes uptake of fructose even in the presence of glucose, and contributes to improvement in efficiency of production of D-lactic acid in a D-lactic acid-producing bacterium. Further, it is unexpected that the efficiency of production of lactic acid is improved by enhancement of expression of fruK alone in a series of fructose metabolism systems, subsequent to uptake of fructose generated from sucrose by the CscA into the cell and metabolism thereof into fructose-1-phosphate.

As the gene of the fructose-1-phosphate kinase (FruK) to be introduced into a host bacterium according to the invention, a DNA having the base sequence of a gene that encodes fructose-1-phosphate kinase (FruK) and that is obtained from an organism possessing this enzyme, or a synthetic DNA sequence synthesized based on a known base sequence of the gene, may be used. Preferable examples thereof include those derived from bacteria belonging to the genus *Escherichia*, bacteria belonging to the genus *Pseudomonas*, bacteria belonging to the genus *Aerobacter*, and bacteria belonging to the genus *Clostridium*, particularly bacteria belonging to the genus *Escherichia*. Examples thereof include a DNA having the base sequence of a gene derived from an *Escherichia coli* MG1655 strain. A DNA having the base sequence of a gene derived from an *Escherichia coli* MG1655 strain is particularly preferable.

The FruR in the invention controls the expression of a group of genes constituting the fructose PTS pathway (i.e., fructose operon), through which the microorganism phosphorylates fructose and incorporate the resultant into the cell. In the case of *Escherichia coli*, a specific example of FruR is a gene having the sequence of 88028 to 89032 of the *Escherichia coli* MG1655 strain genome sequence, which is described in GenBank accession number U00096. Disruption of a FruR gene is known to suppress activity of the synthesis of phosphoenolpyruvic acid (PEP), which is a phosphate donor to fructose; therefore, it is a general expectation that the disruption of a FruR gene will result in failure of fructose uptake into the bacterial cell (see Microbiology Reviews, September, pp. 543-594 (1993)). Accordingly, it is totally unexpected that attenuated expression of fruR may promote uptake of fructose, and it is a totally novel finding that attenuated expression of fruR contributes to an increase in the efficiency of production of D-lactic acid in an D-lactic acid-producing bacterium.

The gene of FruR of which the expression is attenuated in the invention is not limited as long as the gene is an innate gene of the host bacterium, and may be a DNA having the base sequence of the innate gene of the host bacterium that encodes FruR, or a synthetic DNA sequence introduced based on a known base sequence of the FruR gene.

It is more preferable that each of sucrose hydrolase and fructose-1-phosphate kinase (FruK) is obtained by introduction of a gene encoding the corresponding protein derived from *Escherichia coli* O157 or *Escherichia coli* MG1655. Use of genes derived from such bacteria ensures expression of functions.

The "bacterium to which enzymatic activity has been imparted" in the invention refers to a bacterium in which the enzymatic activity has been provided from the outside of the bacterium to the inside of the bacterium by a certain method. Such a bacterium may be prepared, for example by introducing a gene encoding the enzyme or protein from the outside of the bacterium into the inside of the bacterium using a gene recombination technique. Methods for, for example, the preparation of a genomic DNA necessary for the introduction of a gene from the outside of the bacterium into the inside of the bacterium, cleavage and ligation of DNA, transformation, polymerase chain reaction (PCR), and design and synthesis of oligonucleotides used as primers, may be usual methods well known to a person skilled in the art. Those methods are described in, for example, Sambrook, J., et al., "Molecular Cloning A Laboratory Manual, Second Edition", Cold Spring Harbor Laboratory Press, (1989).

The "bacterium in which enzymatic activity is attenuated" in the invention refers to a bacterium in which original activity is deteriorated by a certain method from the outside of the bacterium to the inside of the bacterium, similar to the bacterium to which enzymatic activity has been imparted. The bacterium can be prepared by, for example, disruption of a gene encoding the enzyme or protein (gene disruption).

The "gene disruption" in the invention refers to mutating the base sequence of a certain gene, inserting another DNA into the base sequence of the gene, or deleting a portion of the gene, in order to prevent the function of the gene from being exerted. As a result of gene disruption, the gene cannot be transcribed into mRNA so that translation into a structural gene does not occur, or the gene is transcribed into incomplete mRNA so that the amino acid sequence of the structural protein obtained by translation has mutation or deletion and thus original function thereof cannot be exerted.

Preparation of a gene-disrupted variant may be carried out by any method, as long as a disrupted variant in which expression of the enzyme or protein does not occur can be obtained.] There have been reported a variety of methods for gene disruption (natural breeding, addition of mutagen, UV irradiation, exposure to radiation, random mutation, using transposons, and site-specific gene disruption). From the viewpoint of capability of disrupting only a specific gene, gene disruption by homologous recombination is preferable. Techniques using homologous recombination are described in J. Bacteriol., 161, 1219-1221 (1985) and J. Bacteriol., 177, 1511-1519 (1995) or Proc. Natl. Acad. Sci. U.S.A, 97, 6640-6645 (2000). A person skilled in the art can easily carry out gene disruption by such a method or an application thereof.

The term "*Escherichia coli*" as used in the invention refers to an *Escherichia coli* which can possess ability that produces lactic acid from a plant-derived raw material by using a certain means, irrespective of whether or not the *Escherichia coli* intrinsically has the ability that produces lactic acid from a plant-derived raw material.

The *Escherichia coli* into which the individual genes described above are introduced may be a common *Escherichia coli* which does not have lactic acid-producing ability, and may be any *Escherichia coli* that allows introduction and modification of the individual genes described above. More preferably, the *Escherichia coli* may be an *Escherichia coli* to which lactic acid-producing ability has been imparted in advance, whereby lactic acid can be produced more efficiently. In particular, lactic acid can be efficiently produced from sucrose by imparting sucrose assimilation ability to an *Escherichia coli* that does not intrinsically have sucrose assimilation ability, according to the invention. Examples of the *Escherichia coli* that does not intrinsically have sucrose assimilation ability include strain K12, strain B, strain C and strains derived therefrom.

Examples of the lactic acid-producing bacterium include: an *Escherichia coli* in which pyruvate-formate lyase (Pfl) activity is inactivated or attenuated and *Escherichia coli*-derived NADH-dependent D-lactate dehydrogenase (LdhA) activity is enhanced, which is described in the pamphlet of International Publication No. 2005/033324; an *Escherichia coli* which has the above characteristics and, further, in which FAD-dependent D-lactate dehydrogenase (Dld) activity is inactivated; and an *Escherichia coli* in which malate dehydrogenase (Mdh) activity is inactivated or attenuated, and in which activity of Pfl is inactivated or attenuated, and/or activity of Dld is inactivated or attenuated.

The promoter for expressing individual genes in the invention may be any promoter that can control the expression of any of the above-described genes. The promoter is preferably a strong promoter that constantly functions in a microorganism and of which expression is less susceptible to suppression even in the presence of glucose. Specific examples thereof include a promoter of glyceraldehyde-3-phosphate dehydrogenase (hereinafter sometimes referred to as "GAPDH"), and a promoter of serine hydroxymethyltransferase.

The means for inactivating individual genes to be employed may be selected, without particularly limitations, from means that are commonly used for this purpose. The means may be, for example, gene disruption by homologous recombination or the like.

The method for producing lactic acid according to the invention includes producing lactic acid from a plant-derived sucrose-containing raw material by using the above-described lactic acid-producing bacterium. Specifically, the method includes a process of contacting the lactic acid-producing bacterium with a plant-derived sucrose-containing raw material, and a collection process of collecting lactic acid obtained as a result of the contact.

The plant-derived raw material used in the lactic acid production method may be selected, without particular limitations, from plant-derived sucrose-containing raw materials that are carbon sources obtained from plants. The scope of the plant-derived raw material in the invention encompasses organs such as roots, stems, trunks, branches, leafs, flowers, or seeds, plant bodies including the organs, and decomposition products of the plant organs. Further, carbon sources that are obtained from plant bodies, plant organs, and decomposition products thereof, and that can be used by microorganisms as carbon sources during cultivation are also included in the scope of the plant-derived raw material.

General examples of carbon sources included in the plant-derived raw material include, in addition to sucrose: saccharides such as starch, glucose, fructose, xylose, and arabinose; wood and herbaceous decomposition products containing these saccharide components at high contents; cellulose hydrolysates containing these saccharide components at high contents; and combinations thereof. Further, vegetable oil-derived glycerin or fatty acids may also be included in the scope of the carbon source according to the invention.

The plant-derived raw material in the invention is preferably, for example, an agricultural crop such as a cereal, corn, rice, wheat, soybean, sugarcane, beet, cotton, or a combination thereof. The form thereof when used as a raw material is not particularly limited, and may be an unprocessed material, a juice, a crushed material, or the like. Further, the plant-derived raw material may take a form consisting of the carbon source(s) alone.

The contact between the lactic acid-producing bacterium and the plant-derived raw material in the contact process is generally carried out by culturing the lactic acid-producing bacterium in a medium containing the plant-derived raw material.

The density of the contact between the plant-derived raw material and the lactic acid-producing bacterium may vary depending on the activity of the lactic acid-producing bacterium. In general, the initial sugar concentration (in terms of glucose-equivalent concentration) as the concentration of the plant-derived raw material in the medium may be 20% by mass or lower relative to the total mass of the mixture, and the initial sugar concentration is preferably 15% by mass or lower from the viewpoint of the glucose tolerance of bacterium. Other components may be added in usual amounts for addition to a microbial medium, and the amounts thereof are not particularly limited.

The content of the lactic acid-producing bacterium in the medium may vary depending on the kind and activity of bacterium. In general, the initial bacterial concentration may be from 0.1% by mass to 30% by mass, and preferably from 1% by mass to 10% by mass, relative to the culture liquid, from the viewpoint of controlling culture conditions.

The medium used for culturing lactic acid-producing bacterium is not particularly limited if the medium contains a carbon source, a nitrogen source, an inorganic ion, and organic trace elements, nucleic acids, vitamins, and the like, which are required by the microorganism in order to produce lactic acid.

Examples of carbon sources that are used as appropriate include: saccharides such as glucose, fructose, and molasses; organic acids such as fumaric acid, citric acid, and succinic acid; alcohols such as methanol, ethanol, and glycerol; and other carbon sources. Examples of nitrogen sources that are used as appropriate include: inorganic nitrogen sources such as organic ammonium salts, inorganic ammonium salts, ammonia gas, and aqueous ammonia; organic nitrogen sources such as protein hydrolysates; and other nitrogen sources. Examples of inorganic ions that are used as appropriate and as necessary include magnesium ions, phosphate ions, potassium ions, iron ions, manganese ions, and other inorganic ions.

Examples of organic trace elements that are used as appropriate include: vitamins; amino acids; and yeast extracts, peptone, corn steep liquor, casein decomposition products, and other materials, which include vitamins and amino acids.

The medium to be used in the invention is preferably a liquid medium, considering that application to industrial production.

A preferable example of the medium is a medium added with two or more amino acids. The use of a medium of this kind enables more efficient production of lactic acid. The medium added with two or more amino acids means a medium that includes at least two amino acids from among various naturally-occurring amino acids, and the scope thereof encompasses a medium that includes a hydrolysate of a natural product or natural product extract, such as yeast extract, casamino acid, peptone, whey, blackstrap molasses, and corn steep liquor. In order to obtain more favorable results, a medium that includes at least one selected from yeast extract, peptone, whey, blackstrap molasses, or corn steep liquor, or a mixture thereof, at a content of from 0.5% by mass to 20% by mass is preferable, and the content is more preferably from 2% by mass to 15% by mass. Especially, the addition of corn steep liquor produces a large effect, in which case non-addition of salts such as ammonium sulfate sometime produces better results. The medium is usually a liquid medium.

The culture conditions vary depending on the bacteria prepared and the culture apparatus. In general, the culture temperature during culture is preferably from 20° C. to 40° C., and more preferably from 25° C. to 35° C. The pH during culture is preferably from 4 to 9, more preferably 6.0 to 7.2, and more preferably 6.5 to 6.9, by adjustment with NaOH, $NH_3$, or the like. The culture time is not particularly limited, and is a period of time necessary for the bacteria to grow sufficiently and produce lactic acid.

The culture is generally carried out using a culture vessel capable of controlling the temperature, pH, aerobic conditions, and stirring speed. However, the use of a culture vessel is not essential in the culture according to the invention. In a case in which culture is conducted using a culture vessel, if necessary, seed culture may be carried out in advance as a preculture, and a required amount of the resultant culture may be inoculated into a medium in a culture vessel that has been prepared in advance.

Production of lactic acid by culturing the microorganism obtained in the invention may be carried out without conducting aeration at all; however, aeration is preferably conducted in order to obtain more favorable results. Here, "under aeration conditions" does not necessarily require passage of the air through the culture liquid, and the scope thereof encompasses, depending on the shape of the culture vessel, surface aeration in which an air layer above the culture liquid is substituted while the culture liquid is stirred moderately; "under aeration conditions" refers to allowing an oxygen-containing gas to flow into the culture vessel.

In the case of aeration into the liquid, the dissolved oxygen concentration varies with the combination of internal pressure, stirring blade position, stirring blade shape, and stirring speed. Therefore, the optimal conditions can be determined as follows using lactic acid production efficiency, the amount of organic acids other than lactic acid, or the like as indicators. For example, in a case in which 500 g culture liquid is used for cultivation in a relatively small culture vessel such as a culture apparatus BMJ-01 manufactured by ABLE Corporation, favorable results can be obtained under aeration conditions that can be achieved with a aeration rate of from 0.005 L/min to 0.5 L/min and a stirring speed of from 50 rpm to 500 rpm at normal pressure, more preferably at a aeration rate of from 0.05 L/min to 0.25 L/min and a stirring speed of from 100 rpm to 400 rpm at normal pressure. These aeration/stirring conditions enable oxygen supply at an oxygen-transfer coefficient $K_La$ of from 1/h to 400/h with respect to water at a temperature of 30° C. at normal pressure.

The aeration conditions as described above do not need to be implemented all the time from the start to the end of the culture, and favorable results can also be obtained by implementing the aeration conditions for a part of the duration of the culture process.

In the collection process, lactic acid obtained as a result of the contact is collected. The collection process is usually carried out by collecting lactic acid from the culture product obtained by the cultivation.

The culture product in the invention refers to bacterial cells and a culture liquid that are produced by the method described above, and processed products thereof.

The method of collecting lactic acid from the culture product may be a common known method in the case of collection from, for example, a culture liquid. Examples of methods that can be employed include: a method of removing the bacterial cells by centrifugation or the like, and then acidifying the resultant, and then subjecting the resultant to direct distillation; a method of allowing lactide to form and distilling; a method of adding an alcohol and a catalyst so as to cause esterification, and then distilling the resultant; a method of extracting in an organic solvent; a method of separating using an ion exchange column; a method of concentrating and separating by electrodialysis; and combinations thereof. In addition, since the bacterial cell produced by the method according to the invention produces a group of enzymes suitable for production of lactic acid, production of lactic acid using the bacterial cell and collection of lactic acid produced is also regarded as an embodiment of the method of collecting lactic acid from the culture product.

EXAMPLES

Examples of the invention are described. However, the examples should not be construed as limiting the invention. Unless otherwise indicated, "%" and "part(s)" are based on mass.

Example 1

<Preparation of dld Gene-deleted *Escherichia coli* MG1655 Variant>

The entire base sequence of *Escherichia coli* genomic DNA is known (GenBank accession number: U00096), and the base sequence of a gene encoding FAD-dependent D-lactate dehydrogenase of *Escherichia coli* (hereinafter sometimes referred to as "dld") has also been reported (GenBank accession number: M10038).

Based on the gene information of regions of *Escherichia coli* MG1655 strain genomic DNA adjacent to the dld gene, four kinds of oligonucleotide primer, CAACAC-CAAGCTTTCGCG (SEQ ID NO: 1), TTCCACTCCT-TGTGGTGGC (SEQ ID NO: 2), AACTGCAGAAATTACG-GATGGCAGAG (SEQ ID NO: 3), and TGTTCTAGAAAGTTCTTTGAC (SEQ ID NO: 4), were synthesized.

A genomic DNA of *Escherichia coli* MG1655 strain was prepared according to the method described in Current Protocols in Molecular Biology (John Wiley & Sons). PCR was conducted under usual conditions using the resultant genomic DNA as a template and using the primers of SEQ ID NO: 1 and SEQ ID NO: 2, as a result of which a DNA fragment of about 1.4 kbp (hereinafter sometimes referred to as "dld-L fragment") was amplified. PCR was conducted under usual conditions using the genomic DNA as a template and using the primers of SEQ ID NO: 3 and SEQ ID NO: 4, as a result of which a DNA fragment of about 1.2 kbp (hereinafter sometimes referred to as "dld-R fragment") was amplified. The resultant dld-L fragment was digested with restriction enzymes HindIII and PstI, and the resultant dld-R fragment was digested with restriction enzymes PstI and XbaI. These digested fragments were mixed with a fragment that had been obtained by digesting a temperature-sensitive plasmid pTH18cs1 (Hashimoto-Gotoh, T., et al., Gene, Vol. 241(1), pp 185-191 (2000)) with HindIII and XbaI, and the fragments were ligated using a ligase. Thereafter, DH5α competent cell (DNA-903, Toyobo Co., Ltd.) was transformed with the ligation product, and a transformant that grew on an LB agar plate containing 10 μg/mL chloramphenicol at 30° C. was obtained. The resultant colony was cultured overnight at 30° C. in an LB liquid medium containing 10 μg/mL chloramphenicol. Then, a plasmid was recovered from the resultant bacterial cells. The plasmid obtained was named "pTHΔdld".

Further, the *Escherichia coli* MG1655 strain is available from American Type Culture Collection (ATCC), which is a bank for cells, microorganisms, and genes.

Example 2

A MG1655 strain was transformed with the plasmid pTH-Δdld obtained in Example 1 at 30° C., and a transformant that grew on an LB agar plate containing 10 μg/mL chloramphenicol was obtained. The resultant transformant was applied onto an agar plate, and cultured overnight at 30° C. Next, in order to obtain cultured bacterial cells thereof, the cultured transformant was applied onto an LB agar plate containing 10 μg/mL chloramphenicol, as a result of which a colony that grew at 42° C. was obtained.

Further, the operation of obtaining single colonies that grew at 42° C. was repeated again, thereby selecting a clone in which the entire plasmid was integrated into the chromosome by homologous recombination. It was confirmed that the clone did not have the plasmid in the cytoplasm.

Next, the above-mentioned clone was applied onto an LB agar plate, cultured overnight at 30° C., inoculated into an LB liquid medium (3 mL/test tube), and then cultured with shaking at 42° C. for from 3 hours to 4 hours. This was appropriately diluted (about $10^{-2}$-fold to $10^{-6}$-fold) in order to obtain single colonies, and the diluted liquid was applied onto an LB agar plate, and cultured overnight at 42° C., as a result of which colonies were obtained. From the colonies that appeared, 100 colonies were randomly picked up, and were each allowed to grow on an LB agar plate, and on an LB agar plate containing 10 μg/mL chloramphenicol. Chloramphenicol-sensitive clones that grew only on the LB agar plate were selected. Further, a fragment of about 2.0 kb containing dld was amplified by PCR using the chromosomal DNA of each of these target clones, and a variant in which a dld gene region was deleted was selected. The clone that passed the above selections was considered as a dld-deleted variant, and the resultant variant was named "MG1655Δdld variant".

Example 3

<Preparation of pflB and dld Genes-deleted Variant of *Escherichia coli* MG1655>

The entire base sequence of *Escherichia coli* genomic DNA is known (GenBank accession number: U00096), and the base sequence of a gene encoding pyruvate-formate lyase of *Escherichia coli* (pflB) has also been reported (GenBank accession number: X08035). In order to clone regions adjacent to the base sequence of the pflB gene, four kinds of oligonucleotide primer, GCACGAAAGCTTTGATTACG (SEQ ID NO: 5), TTATTGCATGCTTAGATTTGACTGAAATCG (SEQ ID NO: 6), TTATTGCATGCTTATTTACTGCGTACTTCG (SEQ ID NO: 7), and AAGGCCTACGAAAAGCTGCAG (SEQ ID NO: 8), were synthesized.

PCR was conducted under usual conditions using the genomic DNA of *Escherichia coli* MG1655 strain as a template and using the primers of SEQ ID NO: 5 and SEQ ID NO: 6, as a result of which a DNA fragment of about 1.8 kbp (hereinafter sometimes referred to as "pflB-L fragment") was amplified. PCR was conducted under usual conditions using the genomic DNA of *Escherichia coli* MG1655 strain as a template and using the primers of SEQ ID NO: 7 and SEQ ID NO: 8, as a result of which a DNA fragment of about 1.3 kbp (hereinafter sometimes referred to as "pflB-R fragment") was amplified. These DNA fragments were separated by agarose electrophoresis and recovered, and the pflB-L fragment was digested with HindIII and SphI and the pflB-R fragment was digested with SphI and PstI, respectively. These two kinds of digested fragments and a product obtained by digesting a temperature-sensitive plasmid pTH18cs1 (GenBank accession number: AB019610) with HindIII and PstI were allowed to react in the presence of T4 DNA ligase. Thereafter, an *Escherichia coli* DH5α competent cell (DNA-903, Toyobo Co., Ltd.) was transformed with the ligation product, as a result of which a plasmid containing two fragments—the 5'-upstream adjacent fragment and the 3'-downstream adjacent fragment—of the pflB gene was obtained and named "pTHΔpfl".

The MG1655Δdld variant obtained in Example 2 was transformed with the resultant plasmid pTHΔpfl, and a transformant that grew at 30° C. on an LB agar plate containing 10 μg/mL chloramphenicol was obtained. The resultant transformant was applied onto an agar plate, and cultured overnight at 30° C. Next, in order to obtain cultured bacterial cells thereof, the cultured transformant was applied onto an LB agar plate containing 10 μg/mL chloramphenicol, as a result of which colonies that grew at 42° C. were obtained.

The pfl gene-disrupted MG1655Δdld variant was obtained from the resultant clone according to a method similar to that employed in Example 2 and was named "MG1655ΔpflΔdld variant".

Example 4

<Preparation of *Escherichia coli* MG1655ΔpflΔdldΔmdh Variant>

The entire base sequence of *Escherichia coli* genomic DNA is known (GenBank accession number: U00096), and the base sequence of an mdh gene of *Escherichia coli* has also been reported (Genbank accession number M24777). In order to clone regions adjacent to the base sequence of the mdh gene (939 bp), four kinds of oligonucleotide primer, AAAGGTACCAGAATACCTTCTGCTTTGCCC (SEQ ID NO: 9), AAAGGATCCCCTAAACTCCTTATTATATTG (SEQ ID NO: 10), AAAGGATCCAAACCGGAGCACAGACTCCGG (SEQ ID NO: 11), and AAATCTAGAATCAGATCATCGTCGCCTTAC (SEQ ID NO: 12), were synthesized.

PCR was conducted under usual conditions using the genomic DNA of *Escherichia coli* MG1655 strain as a template and using a primer combination of SEQ ID NO: 9 and SEQ ID NO: 10, as a result of which a DNA fragment of about 800 bp (hereinafter sometimes referred to as "mdh-L fragment") was amplified. PCR was conducted under usual conditions using the genomic DNA of *Escherichia coli* MG1655 strain as a template and using a primer combination of SEQ ID NO: 11 and SEQ ID NO: 12, as a result of which a DNA fragment of about 1000 bp (hereinafter sometimes referred to as "mdh-R fragment") was amplified. These DNA fragments were separated by agarose electrophoresis and recovered. The mdh-L fragment was digested with KpnI and BamHI, and the mdh-R fragment was digested with BamHI and XbaI. These two kinds of digested fragment, and a product obtained by digesting a temperature-sensitive plasmid pTH18cs1 (GenBank accession number: AB019610) with KpnI and XbaI, were allowed to react in the presence of T4 DNA ligase. Thereafter, an *Escherichia coli* DH5α competent cell (DNA-903, Toyobo Co., Ltd.) was transformed with the ligation product, as a result of which a plasmid containing two fragments—the 5'-upstream adjacent fragment and the 3'-downstream adjacent fragment—of the gene encoding mdh was obtained, and the obtained plasmid was named "pTHΔmdh".

The *Escherichia coli* MG1655ΔpflΔdld variant obtained in Example 3 was transformed with the plasmid pTHΔmdh, and an mdh gene-disrupted MG1655ΔpflΔdld variant was prepared according to a method similar to that employed in Example 2. This variant was named "MG1655ΔpflΔdldΔmdh variant".

Example 5

<Preparation of *Escherichia coli* MG1655ΔpflΔdldΔmdhΔasp Variant>

The entire base sequence of *Escherichia coli* genomic DNA is known (GenBank accession number: U00096), and the base sequence of an *Escherichia coli* aspA gene has also been reported (GenBank accession number: X04066). In order to clone regions adjacent to the base sequence of the aspA gene (1,482 bp), four kinds of oligonucleotide primer, TTTTGAGCTCGATCAGGATTGCGTTGGTGG (SEQ ID NO: 13), CGAACAGTAATCGTACAGGG (SEQ ID NO: 14), TACGATTACTGTTCGGCATCGAC- CGAATACCCGAG (SEQ ID NO: 15), and TTTTTCTA-GACCTGGCACGCCTCTCTTCTC (SEQ ID NO: 16), were synthesized.

PCR was conducted under usual conditions using the genomic DNA of *Escherichia coli* MG1655 strain as a template and using a primer combination of SEQ ID NO: 13 and SEQ ID NO: 14, as a result of which a DNA fragment of about 910 bp (hereinafter sometimes referred to as "aspA-L fragment") was amplified. PCR was conducted under usual conditions using the genomic DNA of *Escherichia coli* MG1655 strain as a template and using a primer combination of SEQ ID NO: 15 and SEQ ID NO: 16, PCR, as a result of which a DNA fragment of about 1,100 bp (hereinafter sometimes referred to as "aspA-R fragment") was amplified. These DNA fragments were separated by agarose electrophoresis and recovered. Both of the aspA-L fragment and the aspA-R fragment were terminally blunted with a DNA Blunting Kit (Takara Bio Inc.), and then the 5'-terminals thereof were phosphorylated using T4 polynucleotide kinase according to a conventional method. Separately, a temperature-sensitive plasmid pTH18cs1 was digested with SmaI, and then subjected to dephosphorylation treatment using an alkaline phosphatase. The two kinds of phosphorylated fragment and the dephosphorylated plasmid were allowed to react in the presence of T4 DNA ligase. Thereafter, an *Escherichia coli* DH5α, competent cell (DNA-903, Toyobo Co., Ltd.) was transformed with the ligation product, as a result of which a plasmid containing two fragments—the 5'-upstream adjacent fragment and the 3'-downstream adjacent fragment—of the aspA gene was obtained. This plasmid was named "pTH-Δasp".

The *Escherichia coli* MG1655ΔpflΔdldΔmdh variant obtained in Example 4 was transformed with the plasmid pTHΔasp, and finally aspA gene-disrupted MG1655ΔpflΔdldΔmdh variant was obtained, which was named "MG1655ΔpflΔdldΔmdhΔasp variant". The specific method for obtaining this variant was similar to the method described in Example 2 according to the invention.

Example 6

<Substituting GAPDH Promoter for ldhA Promoter on Genome of *Escherichia coli* MG1655ΔpflΔdldΔmdhΔasp Variant>

The base sequence of the *Escherichia coli* ldhA gene has been already reported (GenBank accession number: U36928). In order to obtain a glyceraldehyde-3-phosphate dehydrogenase (GAPDH) promoter, amplification by a PCR method was carried out using the genomic DNA of *Escherichia coli* MG1655 strain as a template and using AACGAAT-TCTCGCAATGATTGACACGATTC (SEQ ID NO: 17) and ACAGAATTCGCTATTTGTTAGTGAATAAAAGG (SEQ ID NO: 18). The resultant DNA fragment was digested with a restriction enzyme EcoRI, thereby providing a fragment of about 100 bp that encoded a GAPDH promoter. In order to obtain a gene of D-lactate dehydrogenase (ldhA), amplification by a PCR method was carried out using the genomic DNA of *Escherichia coli* MG1655 strain as a template and using GGAATTCCGGAGAAAGTCTTATGAAACT (SEQ ID NO: 19) and CCCAAGCTTTTAAACCAGTTCGT-TCGGGC (SEQ ID NO: 20). The resultant DNA fragment was digested with restriction enzymes EcoRI and HindIII, thereby providing a D-lactate dehydrogenase (ldhA) gene fragment of about 1.0 kbp. The above two DNA fragments were mixed with a fragment obtained by digesting a plasmid pUC18 with restriction enzymes EcoRI and HindIII, and the mixed fragments were ligated using a ligase. Thereafter, an *Escherichia coli* DH5α competent cell (DNA-903, Toyobo Co., Ltd.) was transformed with the ligation product, and a transformant that grew on an LB agar plate containing 50 μg/mL ampicillin was obtained. The resultant colony was cultured in an LB liquid medium containing 50 μg/mL ampicillin overnight at 30° C., and a plasmid pGAP-ldhA was recovered from the resultant bacterial cells.

PCR was carried out using *Escherichia coli* genomic DNA as a template and using AAGGTACCACCAGAGCGTTCT-CAAGC (SEQ ID NO: 21) and GCTCTAGATTCTCCAGT-GATGTTGAATCAC (SEQ ID NO: 22), which were prepared based on the gene information of a 5'-adjacent region of the ldhA gene of the *Escherichia coli* MG1655 strain, thereby amplifying a DNA fragment of about 1000 bp.

Further, PCR was carried out using the plasmid pGAPldhA prepared above as a template and using GGTCTAGAG-CAATGATTCACACGATTCG (SEQ ID NO: 23) prepared based on the sequence information of a glyceraldehyde-3-phophate dehydrogenase (GAPDH) promoter of *Escherichia coli* MG1655 strain, and AACTGCAGGTTCGTTCTCATA-CACGTCC (SEQ ID NO: 24) prepared based on the sequence information of the ldhA gene of *Escherichia coli* MG1655 strain, as a result of which a DNA fragment of about 850 bp that contained a GAPDH promoter and an region of the ldhA gene at or around the initiation codon was obtained.

The fragments obtained above were digested with restriction enzymes KpnI and XbaI, and XbaI and PstI, respectively. The resultant fragments were mixed with a fragment obtained by digesting a temperature-sensitive plasmid pTH18cs1 with KpnI and PstI, and the mixed fragments were ligated using a ligase. Thereafter, a DH5α competent cell (DNA-903, Toyobo Co., Ltd.) was transformed with the ligation product at 30° C., and a transformant that grew on an LB agar plate containing 10 μg/mL chloramphenicol was obtained. The resultant colony was cultured in an LB liquid medium containing 10 μg/mL chloramphenicol overnight at 30° C. Then, a plasmid was recovered from the resultant bacterial cells, and was named "pTH-GAPldhA".

The *Escherichia coli* MG1655ΔpflΔdldΔmdhΔasp variant obtained in Example 5 was transformed with the resultant plasmid pTH-GAPldhA, and cultured on an LB agar plate containing 10 μg/mL chloramphenicol overnight at 30° C., as a result of which a transformant was obtained. The resultant transformant was inoculated into an LB liquid medium containing 10 μg/mL chloramphenicol, and cultured overnight at 30° C. Next, in order to obtain cultured bacterial cells thereof, the cultured transformant was applied onto an LB agar plate containing 10 μg/mL chloramphenicol, as a result of which a colony that grew at 42° C. was obtained. The resultant colony was cultured in an LB liquid medium not containing chloramphenicol overnight at 30° C., and further applied onto an LB agar plate not containing chloramphenicol, as a result of which a colony that grew at 42° C. was obtained.

From the colonies that appeared, 100 colonies were randomly picked up, and were each grown on an LB agar plate not containing chloramphenicol and an LB agar plate containing 10 μg/mL chloramphenicol, and chloramphenicol-sensitive clones were selected. Further, a fragment of about 800 bp containing the GAPDH promoter and the ldhA gene was amplified by PCR using the chromosomal DNA of each of these target clones, and a variant in which the ldhA promoter region was replaced with the GAPDH promoter was selected. The clone that passed the above selections was named "MG1655ΔpflΔdldΔmdhΔasp/GAPldhA genome-inserted variant".

Example 7

<Preparation of *Escherichia coli* MG1655ΔpflΔdldΔmdhΔaspΔfruR/GAPldhA Genome-inserted Variant>

The entire base sequence of *Escherichia coli* genomic DNA is known (GenBank accession number: U00096), and the base sequence of a fruR gene of *Escherichia coli* MG1655 has also been reported. That is, the fruR gene is described at 88028 to 89032 of *Escherichia coli* MG1655 strain genome sequence described at GenBank accession number U00096.

In order to clone regions adjacent to the base sequence of the fruR gene (1005 bp), four kinds of oligonucleotide primer, TACTGCAGATCTCAATAACCGCTATCTGG (SEQ ID NO: 25), GCTCTAGATAGCCATTGTACTGGTATGG (SEQ ID NO: 26), TATCTAGATGCTCAGCCGTAGCTAAGC (SEQ ID NO: 27), and CGAATTCATCCATCTGACATTCGCTGG (SEQ ID NO: 28), were synthesized.

PCR was conducted under usual conditions using the genomic DNA of *Escherichia coli* MG1655 strain as a template and using a primer combination of SEQ ID NO: 25 and SEQ ID NO: 26, as a result of which a DNA fragment of about 950 bp (hereinafter sometimes referred to as "fruR-L fragment") was amplified. PCR was conducted under usual conditions using the genomic DNA of *Escherichia coli* MG1655 strain as a template and using a primer combination of SEQ ID NO: 27 and SEQ ID NO: 28, as a result of which a DNA fragment of about 880 bp (hereinafter sometimes referred to as "fruR-R fragment") was amplified. These DNA fragments were separated by agarose electrophoresis and recovered. The fruR-L fragment was digested with PstI and XbaI, and the fruR-R fragment was digested with XbaI and EcoRI. These two kinds of digested fragment and a product obtained by digesting a temperature-sensitive plasmid pTH18cs1 (GenBank accession number: AB019610) with PstI and EcoRI were allowed to react in the presence of T4 DNA ligase. Thereafter, an *Escherichia coli* DH5α competent cell (DNA-903, Toyobo Co., Ltd.) was transformed with the ligation product, as a result of which a plasmid containing two fragments—the 5'-upstream adjacent fragment and the 3'-downstream adjacent fragment of the fruR gene—was obtained. This plasmid was named "pTHΔfruR".

The *Escherichia coli* MG1655ΔpflΔdldΔmdhΔasp/GAPldhA genome-inserted variant obtained in Example 6 was transformed with the plasmid pTHΔfruR, and a fruR gene-disrupted MG1655ΔpflΔdldΔmdhΔasp/GAPldhA genome-inserted variant was prepared in a manner similar to Example 2. This variant was named "MG1655ΔpflΔdldΔmdhΔaspΔfruR/GAPldhA genome-inserted variant".

Example 8

<Construction of Expression Vector for *Escherichia coli* O157-derived Sucrose Hydrolase (Invertase) Gene and Transformant with the Expression Vector>

The amino acid sequence of invertase of *Escherichia coli* O157 and the base sequence of the gene thereof have been already reported. That is, the invertase-encoding gene (cscA) is described at 3274383 to 3275816 of the *Escherichia coli* O157 strain genome sequence described in GenBank accession number AE005174. At the N-terminal side of the protein encoded by the gene, there is a sequence corresponding to an amino acid sequence that is represented by MTQSRLHAA (SEQ ID NO: 35) in single-letter amino acid code, that has high hydrophobicity, and that is cleaved by a signal peptidase. The promoter sequence of an *Escherichia coli*-derived glyceraldehyde-3-phosphate dehydrogenase (hereinafter sometimes referred to as GAPDH) that is described at 397-440 in the base sequence information of GenBank accession number X02662 may be used as the base sequence of a promoter necessary for expressing the gene.

In order to obtain a GAPDH promoter, amplification by a PCR method was carried out using the genomic DNA of *Escherichia coif* MG1655 strain as a template and using CGAGCTACATATGCAATGATTGACACGATTCCG (SEQ ID NO: 29) and TCTAGAGCTATTTGTTAGTGAATAAAAGG (SEQ ID NO: 30). The resultant DNA fragment was digested with a restriction enzyme NdeI, thereby providing a DNA fragment of about 110 bp corresponding to the GAPDH promoter. The resultant DNA fragment was mixed with a fragment obtained by digesting a plasmid pBR322 (GenBank accession number J01749) with restriction enzymes NdeI and PvuII, and the mixed fragments were ligated using a ligase. Thereafter, a competent cell of *Escherichia coli* DH5α strain (DNA-903, Toyobo Co., Ltd.) was transformed with the ligation product, and a transformant that grew on an LB agar plate containing 50 μg/mL ampicillin was obtained. The resultant colony was cultured in an LB liquid medium containing 50 μg/mL ampicillin overnight at 37° C., and a plasmid pBRgapP was recovered from the resultant bacterial cells.

In order to obtain an invertase gene, amplification by a PCR method was carried out using the genomic DNA (SIGMA-ALDRICH: IRMM449) of *Escherichia coli* O157 as a template and using GATCTAGACGGAGAAAGTCTTATGACGCAATCTCGATTGCATG (SEQ ID NO: 31) and ATGGTACCTTAACCCAGTTGCCAGAGTGC (SEQ ID NO: 32). The resultant DNA fragment was digested with a restriction enzyme XbaI, thereby providing an invertase gene fragment of about 1.4 kbp. The resultant DNA fragment was mixed with a fragment obtained by digesting the plasmid pBRgapP prepared above with restriction enzymes XbaI and PshAI, and the mixed fragments were ligated using a ligase. Thereafter, a competent cell of *Escherichia coli* DH5α strain (DNA-903, Toyobo Co., Ltd.) was transformed with the ligation product, and a transformant that grew on an LB agar plate containing 50 μg/mL ampicillin was obtained. The resultant colony was cultured in an LB liquid medium containing 50 μg/mL ampicillin overnight at 37° C., and a plasmid pGAP-cscA was recovered from the resultant bacterial cells.

A competent cell of MG1655ΔpflΔdldΔmdhΔaspΔfruR/GAPldhA genome-inserted variant prepared in Example 7 was transformed with the plasmid pGAP-cscA, and the resultant transformant was cultured on an Miller's LB Broth agar plate containing 50 μg/mL ampicillin overnight at 37° C., as a result of which an MG1655ΔpflΔdldΔmdhΔaspΔfruR/GAPldhA genome-inserted variant/pGAP-cscA variant was obtained.

Further, a competent cell of MG1655ΔpflΔdldΔmdhΔasp/GAPldhA genome-inserted variant prepared in Example 6 was transformed with the plasmid pGAP-cscA, and the resultant transformant was cultured on an LB Broth, Miller's agar plate containing 50 μg/mL ampicillin overnight at 37° C., as a result of which an MG1655ΔpflΔdldΔmdhΔasp/GAPldhA genome-inserted variant/pGAP-cscA variant was obtained.

Example 9

<Construction of Expression Vector for *Escherichia coli* O157-derived Invertase Gene and *Escherichia coli* MG1655- derived Fructose-1-phosphate Kinase Gene, and Transformant with the Expression Vector>

The amino acid sequence of fructose-1-phosphate kinase of *Escherichia coli* MG1655, and the base sequence of the gene thereof have been already reported. That is, the fructose-1-phosphate kinase-encoding gene (fruK) is described at 2260387 to 2259449 of the *Escherichia coli* MG1655 strain genome sequence described in GenBank accession number U00096.

In order to obtain a fructose-1-phosphate kinase gene, amplification by a PCR method was carried out using the genomic DNA of *Escherichia coli* MG1655 as a template and using ATGGTACCGGAGAAAGTCTTATGAGCAGACGTGTTGCTAC (SEQ ID NO: 33) and TCGGATCCTTATGCCTCTCCTGCTGTCAG (SEQ ID NO: 34). The resultant DNA fragment was digested with a restriction enzyme KpnI, thereby providing a fructose-1-phosphate kinase gene fragment of about 1.0 kbp. The resultant DNA fragment was mixed with a fragment obtained by digesting the plasmid pGAP-cscA constructed in Example 8 with restriction enzymes KpnI and EcoRV, and the mixed fragments were ligated using a ligase. Thereafter, a competent cell of *Escherichia coli* DH5α strain (DNA-903, Toyobo Co., Ltd.) was transformed with the ligation product, and a transformant that grew on an LB agar plate containing 50 μg/mL ampicillin was obtained. The resultant colony was cultured in an LB liquid medium containing 50 μg/mL ampicillin overnight at 37° C., and a plasmid pGAP-cscA-fruK was recovered from the resultant bacterial cells.

A competent cell of MG1655ΔpflΔdldΔmdhΔasp/GAPldhA genome-inserted variant prepared in Example 6 was transformed with the plasmid pGAP-cscA-fruK, and the resultant transformant was cultured on an LB Broth, Miller's agar plate containing 50 μg/mL ampicillin overnight at 37° C., as a result of which an MG1655ΔpflΔdldΔmdhΔasp/GAPldhA genome-inserted variant/pGAP-cscA-fruK variant was obtained.

Example 10

<Production of D-lactic Acid by MG1655ΔpflΔdldΔmdhΔaspΔfruR/GAPldhA Genome-inserted Variant/pGAP-cscA Variant, MG1655ΔpflΔdldΔmdhΔasp/GAPldhA Genome-inserted Variant/pGAP-cscA-fruK Variant, MG1655ΔpflΔdldΔmdhΔasp/GAPldhA Genome-inserted Variant/pGAP-cscA Variant>

MG1655ΔpflΔdldΔmdhΔaspΔfruR/GAPldhA genome-inserted variant/pGAP-cscA variant (hereinafter sometimes referred to as "fruR-disrupted variant" or "ΔfruR variant") obtained in Example 8, MG1655ΔpflΔdldΔmdhΔasp/GAPldhA genome-inserted variant/pGAP-cscA variant (hereinafter sometimes referred to as "cscA variant"), and MG1655ΔpflΔdldΔmdhΔasp/GAPldhA genome-inserted variant/pGAP-cscA-fruK variant (hereinafter sometimes referred to as "fruK-enhanced variant" or "+fruK variant") obtained in Example 9 were respectively seeded into three 500 mL-volume Erlenmeyer flasks that were each equipped with a baffle and each contained 25 mL LB Broth Miller's culture liquid (Difco244620), and cultivation was carried out with stirring overnight at 35° C. and 120 rpm as a preculture. Then, the whole contents of the respective flasks were separately seeded into three 1 L-volume culture vessels (BMJ-01, culture apparatus manufactured by ABLE Corporation) each containing 475 g of the medium shown in Table 1.

TABLE 1

| Medium composition | |
|---|---|
| Sucrose | 12% |
| Corn steep liquor (manufactured by Nihon Shokuhin Kako Co., Ltd.) | 3% |
| Water | Balance |

Cultivation was carried out for 48 hours at an atmospheric pressure, an aeration rate of 0.25 L/min, a stirring speed of 200 rpm, a culture temperature of 35° C., and a pH of 7.4 (adjusted with 24% NaOH). After completing the cultivation, the concentration of lactic acid in the resultant culture liquid was assayed using a high speed liquid chromatography (manufactured by Hitachi, Ltd.) with the following setting. The results are shown in Table 2 and FIG. 1.

Column: ULTRON PS-80H (manufactured by Shinwa Chemical Industries Ltd.)

Eluent: Aqueous perchloric acid solution (pH 2.1)

Flow rate: 1.0 mL/min

Detector: UV detector

Measurement wavelength: 280 nm

TABLE 2

| | MG1655ΔpflΔdldΔmdhΔasp/GAPldhA genome-inserted variant/pGAP-cscA variant (cscA variant) | MG1655ΔpflΔdldΔmdhΔasp/GAPldhA genome-inserted variant/pGAP-cscA-fruK variant (fruK-enhanced variant) | MG1655ΔpflΔdldΔmdhΔaspΔfruR/GAPldhA genome-inserted variant/pGAP-cscA variant (fruR-disrupted variant) |
|---|---|---|---|
| Culture time (hr) | 48 | 48 | 48 |
| Amount of D-lactic acid accumulated (g/L) | 95.5 | 114.6 | 103.6 |
| Sucrose (g/L) | 0 | 0 | 0 |
| Glucose (g/L) | 0 | 2.8 | 3.3 |
| Fructose (g/L) | 14.3 | 10.7 | 0 |

In a known example in which 4 genes (cscA, cscR, cscK, and cscB) of the non-PTS sucrose assimilation pathway including cscA were introduced into *Escherichia coli* and lactic acid was produced from sucrose (Biotechnology Letters. 27, 1891-1896 (2005)), production of 96.5 g of lactic acid took a culture time of 120 hours. In contrast, each of the lactic acid-producing *Escherichia colis* (cscA, fruK-enhanced variant, and fruR-disrupted variant) according to the invention produces a comparable or greater amount of lactic acid by cultivation for only 48 hours. Further, it was demonstrated with regard to sucrose assimilation that lactic acid production time can be greatly reduced by incorporating the activity of only some of the sucrose non-PTS genes, particularly by incorporating only cscA.

In particular, it was demonstrated that introduction of a fruK gene in the presence of cscA resulted in an about 1.2-fold increase in the efficiency of production of D-lactic acid using sucrose as a raw material, and disruption of the fruR gene resulted in an about 1.1-fold increase in the efficiency of production of D-lactic acid.

At this time, the sucrose added at the initiation of the cultivation completely disappeared in all of the variants. Further, it was demonstrated that introduction of fruK gene or disruption of the fruR gene leads to faster assimilation of fructose obtained by the decomposition of sucrose, as compared to a strain that has not been subjected to the gene introduction or gene disruption.

Comparative Example 1

<Production of D-lactic Acid by MG1655ΔpflΔdldΔmdhΔasp/GAPldhA Genome-inserted Variant/pBRgapP Variant>

D-lactic acid production by MG1655ΔpflΔdldΔmdhΔasp/GAPldhA genome-inserted variant/pBRgapP variant was examined in a manner similar to Example 10. This variant is basically the same as the MG1655ΔpflΔdldΔmdhΔasp/GAPldhA genome-inserted variant/pGAP-cscA variant, except that the cscA gene is not contained in the introduced plasmid. The medium composition was also the same as in Example 10; however, sucrose was subjected to filter sterilization prior to use. After cultivation for 48 hours, the concentration of D-lactic acid in the culture liquid was 0 g/L. At this time, the concentrations of glucose and fructose in the culture liquid were also 0 g/L.

From these results, it was confirmed that production of lactic acid through assimilation of sucrose is impossible when a cscA gene is deleted.

Example 11

<Production of D-lactic Acid from Blackstrap Molasses by MG1655ΔpflΔdldΔmdhΔaspΔfruR/GAPldhA Genome-inserted Variant/pGAP-cscA Variant>

Production of D-lactic acid from blackstrap molasses by MG1655ΔpflΔdldΔmdhΔaspΔfruR/GAPldhA genome-inserted variant/pGAP-cscA variant was examined in a manner similar to Example 10.

The entire amount (25 mL) of the same precultured flask contents as the precultured flask contents obtained in Example 10 was seeded into 475 g of the medium shown in Table 3.

TABLE 3

| Medium composition | |
|---|---|
| Blackstrap molasses | 20% |
| Corn steep liquor (manufactured by Nihon Shokuhin Kako Co., Ltd.) | 5% |
| Water | Balance |

Cultivation was carried out at an atmospheric pressure, an aeration rate of 0.25 L/min, a stirring speed of 300 rpm, a culture temperature of 35° C., and a pH of 7.4 (adjusted with 24% NaOH) for 48 hours.

After the cultivation for 48 hours, the concentration of D-lactic acid in the culture liquid was 96.47 g/L. At this time, the concentrations of glucose, fructose, and sucrose in the culture liquid were 0 g/L.

From these results, it was confirmed that lactic acid can be produced from blackstrap molasses as a raw material by using the lactic acid-producing *Escherichia coli* according to the invention.

Example 12

<Construction of Expression Vector for *Bifidobacterium*-derived ldh2 Gene and MG1655Δpfl/pGAP-ldh2 Variant as Transformant with the Expression Vector>

The amino acid sequence of L-lactate dehydrogenase of *Bifidobacterium longum* and the base sequence of the gene thereof have been already reported. That is, the L-lactate dehydrogenase-encoding gene (ldh2) is described at 555 to 1517 of the *Bifidobacterium* genome sequence described in GenBank accession number M33585.

The promoter sequence of *Escherichia coli*-derived glyceraldehyde-3-phosphate dehydrogenase (hereinafter sometimes referred to as GAPDH) that is described at 397-440 in the base sequence information of GenBank accession number X02662 may be used as the base sequence of a promoter necessary for expressing the gene.

In order to obtain a GAPDH promoter, amplification by a PCR method was carried out using the genomic DNA of *Escherichia coli* MG1655 strain as a template and using CGAGCTACATATGCAATGATTGACACGATTCCG (SEQ ID NO: 29) and TCTAGAGCTATTTGTTAGT-GAATAAAAGG (SEQ ID NO: 30). The resultant DNA fragment was digested with a restriction enzyme NdeI, thereby providing a DNA fragment of about 110 bp corresponding to a GAPDH promoter. The resultant DNA fragment was mixed with a fragment obtained by digesting a plasmid pBR322 (GenBank accession number J01749) with restriction enzymes NdeI and PvuII, and the mixed fragments were ligated using a ligase. Thereafter, a competent cell of *Escherichia coli* DH5α strain (DNA-903, Toyobo Co., Ltd.) was transformed with the ligation product, and a transformant that grew on an LB agar plate containing 50 μg/mL ampicillin was obtained. The resultant colony was cultured in an LB liquid medium containing 50 μg/mL ampicillin overnight at 37° C., and a plasmid pBRgapP was recovered from the resultant bacterial cells.

In order to obtain an L-lactate dehydrogenase gene, amplification by a PCR method was carried out using *Bifidobacterium longum* (ATCC 15707) as a template and using AATCTAGACGGAGAAAGTCTTATGGCG-GAAACTACCGTTAAGC (SEQ ID NO: 36) and CTGTCTAGATCAGAAGCCGAACTGGGCG (SEQ ID NO: 37). The resultant DNA fragment was digested with a restriction enzyme XbaI, thereby providing an L-lactate dehydrogenase gene fragment of about 1.0 kbp. The resultant DNA fragment was mixed with a fragment obtained by digesting the plasmid pBRgapP prepared above with a restriction enzyme XbaI, and the mixed fragments were ligated using a ligase. Thereafter, a competent cell of *Escherichia coli* DH5α strain (DNA-903, Toyobo Co., Ltd.) was transformed with the ligation product, and a transformant that grew on an LB agar plate containing 50 μg/mL ampicillin was obtained. The resultant colony was cultured in an LB liquid medium containing 50 μg/mL ampicillin overnight at 37° C., and a plasmid pGAP-ldh2 was recovered from the resultant bacterial cells.

A competent cell of MG1655 strain in which a pfl gene had been deleted by using pTHΔpfl prepared in Example 3 in a manner similar to Example 2 (referred to as "MG1655Δpfl variant") was transformed with the plasmid pGAP-ldh2, and the resultant transformant was cultured on an Miller's LB Broth agar plate containing 50 μg/mL ampicillin overnight at 37° C., as a result of which an MG1655Δpfl/pGAP-ldh2 variant was obtained.

Example 13

<Production of L-lactic Acid by MG1655Δpfl/pGAP-ldh2 Variant>

L-lactic acid production from glucose by MG1655Δpfl/pGAP-ldh2 variant obtained in Example 12 was examined in a manner similar to Example 10.

25 mL of flask contents that had been precultured in the same manner as the precultures obtained in Example 10 was seeded into 475 g of the medium shown in Table 4 below.

TABLE 4

| Glucose | 12% |
| Yeast extract (manufactured by Difco Laboratories Inc.) | 3% |
| Water | Balance |

Cultivation was carried out at an atmospheric pressure, an aeration rate of 0.25 L/min, a stirring speed of 200 rpm, a culture temperature of 35° C., and a pH of 7.5 (adjusted with 24% NaOH) for 18 hours.

After the cultivation for 18 hours, the concentration of L-lactic acid in the culture liquid was 97.02 g/L.

From these results, it was confirmed that L-lactic acid can be produced from glucose by using the Bifidobacterium-derived L-lactate dehydrogenase.

Example 14

<Preparation of MG 1655 ΔpflΔdldΔmdhΔasp/GAPldhA Genome-inserted Variant/pGAP-ldh2 Variant>

A transformant in which the pGAP-ldh2 plasmid prepared in Example 12 was introduced into the D-lactic acid-producing variant prepared in Example 6 was prepared. Specifically, the following procedure was used.

A competent cell of MG1655ΔpflΔdldΔmdhΔasp/GAPldhA genome-inserted variant prepared in Example 6 was transformed with the plasmid pGAP-ldh2. The resultant transformant was cultured on an Miller's LB Broth agar plate containing 50 μg/mL ampicillin overnight at 37° C., as a result of which an MG1655ΔpflΔdldΔmdhΔasp/GAPldhA genome-inserted variant/pGAP-ldh2 variant was obtained.

Example 15

<Production of L-lactic Acid by MG1655ΔpflΔdldΔmdhΔasp/GAPldhA Genome-inserted Variant/pGAP-ldh2 Variant>

L-lactic acid production from glucose by MG1655ΔpflΔdldΔmdhΔasp/GAPldhA genome-inserted variant/pGAP-ldh2 variant obtained in Example 14 was examined in a manner similar to Example 13.

Cultivation was carried out at an atmospheric pressure, an aeration rate of 0.25 L/min, a stirring speed of 200 rpm, a culture temperature of 35° C., and a pH of 7.5 (adjusted with 24% NaOH) for 18 hours.

After the cultivation for 18 hours, the concentration of L-lactic acid in the culture liquid was 116.84 g/L.

From these results, it was confirmed that L-lactic acid can be produced from glucose as a raw material by using an Escherichia coli variant for production of D-lactic acid. The production of L-lactic acid was confirmed by measuring the amount of L-lactic acid and the amount of D-lactic acid, using a F-Kit D-/L-lactic acid (Product code 1112821, J.K. International Inc.).

Example 16

<Preparation of MG1655ΔpflΔmdhΔaspΔlldDΔldhA/GAPldh2 Genome-inserted Variant and MG1655 ΔpflΔmdhΔaspΔlldDΔldhAΔfruR/GAPldh2 Genome-inserted Variant>

An Escherichia coli variant for L-lactic acid production was prepared by substituting the ldh2 gene for the ldhA gene of the Escherichia coli variant for D-lactic acid production used in Example 6 (MG1655ΔpflΔdldΔmdhΔasp/GAPldhA genome-inserted variant) and disrupting lldD, which is a gene of an enzyme catalyzing the decomposition of L-lactic acid. Further, a fruR-disrupted Escherichia coli variant for L-lactic acid production was prepared by disrupting a fruR gene. Specifically, the following procedure was used.

(Preparation of ldhA Gene-disrupted Variant)

Based on the gene information of regions of MG1655 genomic DNA adjacent to the ldhA gene, four kinds of oligonucleotide primer, AAGGTACCACCAGAGCGTTCT-CAAGC (SEQ ID NO: 21), GCTCTAGATTCTCCAGT-GATGTTGAATCAC (SEQ ID NO: 22), GCTCTAGAGCATTCCTGACAGCAGAAGC (SEQ ID NO: 38) and AACTGCAGTCGGCGTGTAGTAGTGAACC (SEQ ID NO: 39), were synthesized. Using these primers, a plasmid pTHΔldhA for gene disruption was constructed according to a method similar to that employed in Example 1. Further, a competent cell of MG1655ΔpflΔdldΔmdhΔasp/GAPldhA genome-inserted variant was transformed with the pTHΔldhA, and an ldhA-deleted variant was selected according to a method similar to that employed in Example 2. The resultant variant was named "MG1655ΔpflΔdldΔmdhΔasp/GAPldhA genome-inserted ΔldhA variant".

(Preparation of dld Gene Revertant)

Based on the gene information of regions of Escherichia coli MG1655 genomic DNA adjacent to the dld gene, two kinds of oligonucleotide primer, CAACAC-CAAGCTTTCGCG (SEQ ID NO: 40) and TGTTCTA-GAAAGTTCTTTGAC (SEQ ID NO: 41), were synthesized. PCR was carried out using these primers and the genomic DNA of Escherichia coli MG1655 as a template, and the resultant DNA fragment was cleaved with restriction enzymes HindIII and XbaI. Further, a plasmid pTH18cs1 was cleaved with restriction enzymes HindIII and XbaI, and mixed with the dld fragment. Thereafter, the fragments were ligated using a ligase, thereby providing a plasmid pTHDLD. Further, a competent cell of MG1655ΔpflΔdldΔmdhΔasp/GAPldhA genome-inserted variant was transformed with the pTHDLD, and a dld revertant was selected according to a method similar to that employed in Example 2. The resultant variant was named "MG1655ΔpflΔmdhΔasp/GAPldhA genome-inserted ΔldhA variant".

(Preparation of lldD Gene-disrupted Variant)

Based on the gene information of regions of MG1655 strain genomic DNA adjacent to the lldD gene, four kinds of oligonucleotide primer, GGAAGCTTCAAATTG-GCGTCTCTGATCT (SEQ ID NO: 42), AAACCCGGGC-CATCCATATAGTGGAACAGGAACGG (SEQ ID NO: 43), GGGCTCGAGTGGCGATGACGCTGACTGG (SEQ ID NO: 44) and CGTCTAGAACGGGTAAATCTGGTGGT-GACCGTCACCCG (SEQ ID NO: 45), were synthesized. Using these primers, a plasmid pTHΔlldD for gene disruption was constructed according to a method similar to that employed in Example 1. Further, a competent cell of MG1655ΔpflΔmdhΔasp/GAPldhA genome-inserted ΔldhA variant was transformed with the pTHΔlldD, and an lldD-deleted variant was selected according to a method similar to that employed in Example 2. The resultant variant was named "MG1655ΔpflΔmdhΔaspΔlldD/GAPldhA genome-inserted ΔldhA variant".

(Preparation of Ldh2 Gene Genome-inserted Variant)

The amino acid sequence of L-lactate dehydrogenase of *Bifidobacterium longum* and the base sequence of the gene thereof have been already reported. That is, the L-lactate dehydrogenase-encoding gene (ldh2) is described at 555 to 1517 of the *Bifidobacterium* genome sequence described in GenBank accession number M33585.

In order to obtain a gene (ldh2) encoding L-lactate dehydrogenase, two kinds of oligonucleotide primer, AAGAAT-TCCGGAGAAAGTCTTATGGCGGAAAC-TACCGTTAAGC (SEQ ID NO: 46), CTGTCTAGATCAGAAGCCGAACTGGGCG (SEQ ID NO: 47), were synthesized using the genomic DNA of *Bifidobacterium longum* (ATCC15707) as a template. PCR was carried out using these primers, and the resultant DNA fragment was cleaved with restriction enzymes EcoRI and XbaI.

In order to obtain a GAPDH promoter, two kinds of oligonucleotide primer, GGTCTAGAGCAATGATTGACAC-GATTCCG (SEQ ID NO: 48) and CGGAATTCCGC-TATTTGTTAGTGAATAAAAG (SEQ ID NO: 49), were synthesized using the genomic DNA of *Escherichia coli* MG1655 strain as a template. The resultant DNA fragment was cleaved with restriction enzymes EcoRI and XbaI.

A plasmid obtained by cleaving the pTHΔldhA obtained above with XbaI, and the EcoRI-XbaI fragment of the *Bifidobacterium longum*-derived ldh2 and the EcoRI-XbaI fragment of the *Escherichia coli*-derived GAPDH promoter obtained above, were mixed, and the fragments were ligated using a ligase. Thereafter, a competent cell of *Escherichia coli* DH5α strain (DNA-903, Toyobo Co., Ltd.) was transformed with the ligation product, and a transformant that grew on an LB agar plate containing 50 μg/mL ampicillin was obtained. The resultant colony was cultured in an LB liquid medium containing 50 μg/mL ampicillin overnight at 37° C., and a plasmid pTHΔldhA::GAPLDH2 was recovered from the resultant bacterial cells. An MG1655ΔpflΔmdhΔaspΔlld/GAPldhA genome-inserted ΔldhA variant was transformed with the resultant plasmid, and an ldh2 genome-inserted variant was selected based on PCR amplification of ldh2 according to a method similar to that employed in Example 2.

The resultant variant was named "MG1655ΔpflΔmdhΔaspΔlldDΔldhA/GAPldh2 genome-inserted variant".

(Preparation of fruR Gene-disrupted Variant)

An MG1655ΔpflΔmdhΔaspΔlldDΔldhA/GAPldh2 genome-inserted variant was transformed with the plasmid pTHΔfruR prepared in Example 7, and an MG1655ΔpflΔmdhΔaspΔlldDΔldhA/GAPldh2 genome-inserted variant in which the fruR gene was disrupted was obtained according to a method similar to that employed in Example 2. This variant was named "MG1655ΔpflΔmdhΔaspΔlldDΔldhAΔfruR/GAPldh2 genome-inserted variant".

Example 17

<Preparation of MG1655ΔpflΔmdhΔaspΔlldDΔldhA/GAPldh2 Genome-inserted/pGAP-cscA Variant and MG1655ΔpflΔmdhΔaspΔlldDΔldhAΔfruR/GAPldh2 Genome-inserted/pGAP-cscA Variant>

The expression vector for the sucrose hydrolase (invertase) gene was introduced into each of the *Escherichia coli* variant for L-lactic acid production and the fruR-disrupted *Escherichia coli* variant for L-lactic acid production, which were prepared in Example 16, thereby preparing an *Escherichia coli* variant producing L-lactic acid from sucrose. Specifically, the following procedure was used.

Competent cells of MG1655ΔpflΔmdhΔaspΔlldDΔldhA/GAPldh2 genome-inserted variant and MG1655ΔpflΔmdhΔaspΔlldDΔldhAΔfruR/GAPldh2 genome-inserted variant prepared in Example 16 were transformed with the plasmid pGAP-cscA prepared in Example 8, and the resultant transformant of each variant was cultured on an Miller's LB Broth agar plate containing 50 μg/mL ampicillin overnight at 37° C., as a result of which an MG1655ΔpflΔmdhΔaspΔlldDΔldhA/GAPldh2 genome-inserted/pGAP-cscA variant and an MG1655ΔpflΔmdhΔaspΔlldDΔldhAΔfruR/GAPldh2 genome-inserted/pGAP-cscA variant were obtained.

Example 18

<Preparation of MG1655ΔpflΔmdhΔaspΔlldDΔldhA/GAPldh2 Genome-inserted/pGAP-cscA-fruK Variant>

The *Escherichia coli* variant for L-lactic acid production prepared in Example 16 was transformed with the expression vector for the sucrose hydrolase (invertase) and fructose-1-phosphate kinase genes, thereby providing an L-lactic acid-producing fruK-enhanced *Escherichia coli* variant. Specifically, the following procedure was used.

A competent cell of MG1655ΔpflΔmdhΔaspΔlldDΔldhA/GAPldh2 genome-inserted variant prepared in Example 16 was transformed with the plasmid pGAP-cscA-fruK prepared in Example 9, and the resultant transformant was cultured on an Miller's LB Broth agar plate containing 50 μg/mL ampicillin overnight at 37° C., as a result of which an MG1655ΔpflΔmdhΔaspΔlldDΔldhA/GAPldh2 genome-inserted/pGAP-cscA-fruK variant was obtained.

Example 19

<Production of L-lactic Acid by MG1655 ΔpflΔmdhΔasp-ΔlldDΔldhA/GAPldh2 Genome-inserted/pGAP-cscA Variant, MG1655 ΔpflΔmdhΔaspΔlldDΔldhAΔfruR/GAPldh2 Genome-inserted/pGAP-cscA Variant, and MG1655 ΔpflΔmdhΔaspΔlldDΔldhA/GAPldh2 Genome-inserted/pGAP-cscA-fruK Variant>

L-lactic acid production from blackstrap molasses by MG1655ΔpflΔmdhΔaspΔlldDΔldhA/GAPldh2 genome-inserted/pGAP-cscA variant, MG1655ΔpflΔmdhΔaspΔlldDΔldhAΔfruR/GAPldh2 genome-inserted/pGAP-cscA variant, and MG1655ΔpflΔmdhΔaspΔlldDΔldhA/GAPldh2 genome-inserted/pGAP-cscA-fruK variant was examined.

The MG1655 ΔpflΔmdhΔaspΔlldDΔldhA/GAPldh2 genome-inserted/pGAP-cscA variant, the MG1655ΔpflΔmdhΔaspΔlldDΔldhAΔfruR/GAPldh2 genome-inserted/pGAP-cscA variant, and the MG1655ΔpflΔmdhΔaspΔlldDΔldhA/GAPldh2 genome-inserted/pGAP-cscA-fruK variant obtained in Example 17 and Example 18 were respectively seeded into 500 mL-volume Erlenmeyer flasks that were each equipped with a baffle and each contained 50 mL of the preculture medium shown in Table 5, and cultivation was carried out with stirring overnight at 35° C. and 120 rpm as a preculture. Then, 25 mL of the precultured contents of each flask was individually seeded into 475 g of the medium shown in Table 6 below, and cultivation experiments were carried out in a manner similar to Example 10.

TABLE 5

Preculture medium composition

| | |
|---|---|
| Blackstrap molasses | 2% |
| Corn steep liquor (manufactured by Nihon Shokuhin Kako Co., Ltd.) | 10% |
| Water | Balance | pH 7.8 after autoclaving (adjusted by 24% NaOH)

TABLE 6

Medium composition

| | |
|---|---|
| Blackstrap molasses | 20% |
| Corn steep liquor (manufactured by Nihon Shokuhin Kako Co., Ltd.) | 5% |
| Water | Balance |

Cultivation was carried out at an atmospheric pressure, an aeration rate of 0.25 L/min, a stirring speed of 350 rpm, a culture temperature of 35° C., and a pH of 7.5 (adjusted with 24% NaOH) for 24 hours.

After the cultivation for 24 hours, the concentration of L-lactic acid in the culture liquid was 75.12 g/L in the case of MG1655ΔpflΔmdhΔaspΔlldDΔldhA/GAPldh2 genome-inserted/pGAP-cscA variant (cscA), 83.79 g/L in the case of MG1655 ΔpflΔmdhΔaspΔlldDΔldhAΔfruR/GAPldh2 genome-inserted/pGAP-cscA variant (fruR-disrupted variant), and 84.32 g/L in the case of MG1655 ΔpflΔmdhΔasp-ΔlldDΔldhA/GAPldh2 genome-inserted/pGAP-cscA-fruK variant (fruK-enhanced variant), respectively.

From these results, it was confirmed that L-lactic acid can be produced from blackstrap molasses as a raw material by using the lactic acid-producing *Escherichia coli* according to the invention. Further, it was demonstrated that disruption of the fruR gene of the lactic acid-producing *Escherichia coli* improves the efficiency of production of L-lactic acid. Further, it was demonstrated that enhancement of the fruK gene of the lactic acid-producing *Escherichia coli* also improves the efficiency of production of L-lactic acid.

Comparative Example 2

<Construction of Expression Vector for *Escherichia coli* O157-derived Invertase Gene and *Zymomonas*-derived Glucose Transport-promoting Protein (glf) Gene, and Transformant with the Expression Vector>

The base sequence of *Escherichia coli* GAPDH gene has been already reported. In order to obtain a glyceraldehyde-3-phosphate dehydrogenase (GAPDH) promoter, a primer having the base sequence of CCAAGCTTCTGCAGGTC-GACGGATCCGAGCTCAGCTATTTGTTAGTGAATAAAAG (SEQ ID NO: 50) was synthesized. A DNA fragment was amplified by a PCR method using the genomic DNA of *Escherichia coli* MG1655 strain as a template and using a primer combination of SEQ ID NO: 50 and SEQ ID NO: 29. The primer of SEQ ID NO: 29 has an NdeI recognition site at its 5'-terminal side, and the primer of SEQ ID NO: 50 has HindIII, PstI, SalI, BamHI, and Sad recognition sites in this order from its 5'-terminal side. The resultant DNA fragment was digested with restriction enzymes NdeI and HindIII, thereby providing a GAPDH promoter-encoding fragment of about 100 bp. Next, the above DNA fragment was mixed with an *Escherichia* colt cloning vector pBR322 (GenBank accession number 101749) that has been digested with NdeI and HindIII, and the fragments were ligated using a ligase. Thereafter, an *Escherichia coli* DH5α competent cell (manufactured by Takara Bio Inc.) was transformed with the ligation product, and a transformant that grew on an LB agar plate containing 50 μg/mL ampicillin was obtained. The resultant colony was cultured in an LB liquid medium containing 50 μg/mL ampicillin overnight at 30° C., and a plasmid was recovered from the resultant bacterial cells. This plasmid was named "pGAP".

A competent cell of MG1655ΔpflΔdldΔmdhΔasp/GA-PldhA genome-inserted variant prepared in Example 6 was transformed with the plasmid pGAP-cscA-glf, and the resultant transformant was cultured on an Miller's LB Broth agar plate containing 50 μg/mL ampicillin overnight at 37° C., as a result of which an MG1655ΔpflΔdldΔmdhΔasp/GAPldhA genome-inserted variant/pGAP-cscA-glf variant was obtained.

The base sequence of an invertase gene (cscA) of *Escherichia coli* O157 strain has been already reported. That is, the invertase gene (cscA) is described at 3274383 to 3275816 of the *Escherichia coli* O157 strain genome sequence described in GenBank accession number AE005174. In order to obtain the cscA gene, primers respectively having base sequences of GCGGATCCGCTGGTGGAATATATGACG-CAATCTCGATTGC (SEQ ID NO: 51) and GACGCGTC-GACTTAACCCAGTTGCCAGAGTGC (SEQ ID NO: 52) were prepared. The primer of SEQ ID NO: 51 has a BamHI recognition site and a 13 base-long ribosome binding sequence of the GAPDH gene in this order from its 5'-terminal side. The primer of SEQ ID NO: 52 has a SalI recognition site at its 5'-terminal side. PCR was carried out under usual conditions using the two kinds of primer described above and using the genomic DNA (SIGMA-ALDRICH:IRMM449) of *Escherichia coli* O157 strain as a template, and the resultant DNA fragment was digested with restriction enzymes BamHI and SalI, thereby providing an invertase gene (cscA) fragment of about 1.4 kbp. This DNA fragment was mixed with a fragment obtained by digesting a plasmid pGAP with restriction enzymes BamHI and SalI, and the mixed fragments were ligated using a ligase. Thereafter, an *Escherichia coli* DH5α competent cell (manufactured by Takara Bio Inc.) was transformed with the ligation product, and a transformant that grew on an LB agar plate containing 50 μg/mL ampicillin was obtained. The resultant colony was cultured in an LB liquid medium containing 50 μg/mL ampicillin overnight at 30° C., and a plasmid pGAP-cscA was recovered from the resultant bacterial cells. In this way, an expression vector for the invertase gene (cscA) was constructed.

The base sequence of a sugar-transporting enzyme glucose transport-promoting protein gene (glf) of *Zymomonas mobilis* (ATCC 29191) has been already reported (GenBank accession number M60615). In order to obtain the glf gene, primers respectively having the base sequence of CCTGTC-GACGCTGGTGGAATATATGAGTTCT-GAAAGTAGTCAGG (SEQ ID NO: 53) and CTACTG-CAGCTACTTCTGGGAGCGCCACA (SEQ ID NO: 54) were prepared. The primer of SEQ ID NO: 53 has a SalI recognition site and a 13 base-long ribosome binding sequence of the GAPDH gene in this order from its 5'-terminal side. The primer of SEQ ID NO: 54 has a PstI recognition site at its 5'-terminal side. PCR was carried out under usual conditions using the two kinds of primer and the genomic DNA of *Zymomonas* mobilis as a template, and the resultant DNA fragment was digested with restriction enzymes SalI and PstI, thereby providing a sugar-transporting enzyme glucose transport-promoting protein gene (glf) fragment of about 1.4 kbp. This DNA fragment was mixed with a fragment obtained by digesting a plasmid pGAP-cscA with restriction enzymes SalI and PstI, and the mixed fragments were ligated using a ligase. Thereafter, an *Escherichia coli* DH5α competent cell (manufactured by Takara Bio Inc.) was transformed with the ligation product, and a transformant that grew on an LB agar plate containing 50 μg/mL ampicillin was obtained. The resultant colony was cultured in an LB liquid medium containing 50 μg/mL ampicillin overnight at 30° C., and a plasmid pGAP-cscA-glf was recovered from the resultant bacterial cells. In this way, an expression vector for the invertase (cscA) gene and the glucose transport-promoting protein (glf) gene was constructed.

<Production of D-lactic Acid by MG1655ΔpflΔdldΔmdhΔasp/GAPldhA Genome-inserted Variant/pGAP-cscA-glf Variant, MG1655ΔpflΔdldΔmdhΔasp/GAPldhA Genome-inserted Variant/pGAP-cscA Variant>

The MG1655ΔpflΔdldΔmdhΔasp/GAPldhA genome-inserted variant/pGAP-cscA-glf variant was seeded into a test tube containing 3 mL of Miller's LB Broth culture liquid (Difco244620), and cultivation was carried out with stirring at 30° C. and 200 rpm for 9 hours as a preculture.

Then, 100 μL of a preculture liquid was seeded into each of four 100 mL Erlenmeyer flasks, each of which was equipped with a baffle, added with 10 g of $CaCO_3$ (first grade, Junsei Chemical Co., Ltd.) and sterilized in advance, and contained 20 mL of the medium shown in Table 7. Cultivation was carried out with stirring at 35° C. and 90 rpm for 48 hours. As a control, the cscAMG1655ΔpflΔdldΔmdhΔasp/GAPldhA genome-inserted variant/pGAP-cscA variant described in Example 10 was cultivated in the same manner. After completing the cultivation, the concentration of lactic acid in the resultant culture liquid was assayed according to the method described in Example 10.

After the cultivation for 48 hours, the concentration of D-lactic acid in the culture liquid was 48.9 g/L in the case of cscA, and 9.3 g/L in the case of MG1655ΔpflΔdldΔmdhΔasp/GAPldhA genome-inserted variant/pGAP-cscA-glf variant.

From these results, it was demonstrated that an effect in terms of improving the efficiency of production of lactic acid is not observed when uptake of sugar is enhanced by using a glucose transport-promoting protein gene (glf), which is, similarly to cscA, involved in the sugar metabolism system.

TABLE 7

| Medium composition | |
|---|---|
| Sucrose | 10% |
| Corn steep liquor (manufactured by Nihon Shokuhin Kako Co., Ltd.) | 5% |
| Water | Balance |

Adjusted to pH 8.0 by NaOH

Disclosures of Japanese Patent Application No. 2008-237177 filed on Sep. 16, 2008 and Japanese Patent Application No. 2009-32043 filed on Feb. 13, 2009 are incorporated herein by reference in their entirety.

All publications, patent applications, and technical standards mentioned in this specification are herein incorporated by reference to the same extent as if each individual publication, patent application, or technical standard was specifically and individually indicated to be incorporated by reference.

What is claimed is:

1. A lactic acid-producing *Escherichia coli* comprising at least one gene of a sucrose non-PTS gene group, including at least a sucrose hydrolase gene, provided that a combination of a repressor protein (cscR), a sucrose hydrolase (cscA), a fructokinase (cscK) and a sucrose permease (cscB) and a combination of a sucrose hydrolase (cscA), a fructokinase (cscK) and a sucrose permease (cscB) are excluded,
wherein the lactic acid-producing *Escherichia coli* comprises a lactic acid production enhancing system provided by genetic recombination and a fructose metabolism ability improvement system, and wherein
the fructose metabolism ability improvement system is enhancement of phosphorylation ability derived from fructose-1-phosphate kinase activity or
the fructose metabolism ability improvement system is enhancement of fructose uptake ability in a fructose metabolism pathway derived from inactivation or attenuation of innate FruR activity of the *Escherichia coli*.

2. The lactic acid-producing *Escherichia coli* according to claim 1, wherein the lactic acid-producing *Escherichia coli* comprises only the sucrose hydrolase gene from among the sucrose non-PTS gene group, and the lactic acid-producing *Escherichia coli* comprises the lactic acid production enhancing system provided by genetic recombination.

3. The lactic acid-producing *Escherichia coli* according to claim 1, wherein the lactic acid production enhancing system includes inactivation or attenuation of pyruvate-formate lyase activity.

4. The lactic acid-producing *Escherichia coli* according to claim 1, wherein the lactic acid production enhancing system includes enhancement of NADH-dependent lactate dehydrogenase activity for producing D-lactic acid or L-lactic acid.

5. The lactic acid-producing *Escherichia coli* according to claim 1, wherein the lactic acid production enhancing system comprises enhancement of D-lactate dehydrogenase activity and inactivation or attenuation of innate FAD-dependent D-lactate dehydrogenase activity of the *Escherichia coli*.

6. The lactic acid-producing *Escherichia coli* according to claim 1, wherein the lactic acid production enhancing system comprises enhancement of L-lactate dehydrogenase activity and inactivation or attenuation of at least one of innate D-lactate dehydrogenase activity of the *Escherichia coli* or innate FMN-dependent L-lactate dehydrogenase activity of the *Escherichia coli*.

7. The lactic acid-producing *Escherichia coli* according to claim 1, wherein the sucrose hydrolase gene is derived from a bacterium belonging to the genus *Escherichia*.

8. The lactic acid-producing *Escherichia coli* according to claim 1, wherein the sucrose hydrolase gene is derived from an *Escherichia coli* O157 bacterium.

9. The lactic acid-producing *Escherichia coli* according to claim 1, wherein the fructose-1-phosphate kinase is derived from a bacterium belonging to the genus *Escherichia*.

10. The lactic acid-producing *Escherichia coli* according to claim 1, wherein the fructose-1-phosphate kinase is a protein derived from *Escherichia coli* MG1655.

11. The lactic acid-producing *Escherichia coli* according to claim 1, wherein the lactic acid-producing *Escherichia coli* is a variant derived from *Escherichia coli* K12.

12. A method for producing lactic acid, the method comprising:
   producing lactic acid from a plant-derived sucrose-containing raw material by using the lactic acid-producing *Escherichia coli* of claim 1.

* * * * *

SEQUENCE LISTING

```
<160> NUMBER OF SEQ ID NOS: 54

<210> SEQ ID NO 1
<211> LENGTH: 18
<212> TYPE: DNA
<213> ORGANISM: Artificial
<220> FEATURE:
<223> OTHER INFORMATION: primer

<400> SEQUENCE: 1
caacaccaag ctttcgcg                                                   18

<210> SEQ ID NO 2
<211> LENGTH: 19
<212> TYPE: DNA
<213> ORGANISM: Artificial
<220> FEATURE:
<223> OTHER INFORMATION: primer

<400> SEQUENCE: 2
ttccactcct tgtggtggc                                                  19

<210> SEQ ID NO 3
<211> LENGTH: 26
<212> TYPE: DNA
<213> ORGANISM: Artificial
<220> FEATURE:
<223> OTHER INFORMATION: primer

<400> SEQUENCE: 3
```

```
aactgcagaa attacggatg gcagag                                    26

<210> SEQ ID NO 4
<211> LENGTH: 21
<212> TYPE: DNA
<213> ORGANISM: Artificial
<220> FEATURE:
<223> OTHER INFORMATION: primer

<400> SEQUENCE: 4
tgttctagaa agttctttga c                                         21

<210> SEQ ID NO 5
<211> LENGTH: 20
<212> TYPE: DNA
<213> ORGANISM: Artificial
<220> FEATURE:
<223> OTHER INFORMATION: primer

<400> SEQUENCE: 5
gcacgaaagc tttgattacg                                           20

<210> SEQ ID NO 6
<211> LENGTH: 30
<212> TYPE: DNA
<213> ORGANISM: Artificial
<220> FEATURE:
<223> OTHER INFORMATION: primer

<400> SEQUENCE: 6
ttattgcatg cttagatttg actgaaatcg                                30

<210> SEQ ID NO 7
<211> LENGTH: 30
<212> TYPE: DNA
<213> ORGANISM: Artificial
<220> FEATURE:
<223> OTHER INFORMATION: primer

<400> SEQUENCE: 7
ttattgcatg cttatttact gcgtacttcg                                30

<210> SEQ ID NO 8
<211> LENGTH: 21
<212> TYPE: DNA
<213> ORGANISM: Artificial
<220> FEATURE:
<223> OTHER INFORMATION: primer

<400> SEQUENCE: 8
aaggcctacg aaaagctgca g                                         21

<210> SEQ ID NO 9
<211> LENGTH: 30
<212> TYPE: DNA
<213> ORGANISM: Artificial
<220> FEATURE:
<223> OTHER INFORMATION: primer

<400> SEQUENCE: 9
aaaggtacca gaataccttc tgctttgccc                                30

<210> SEQ ID NO 10
<211> LENGTH: 30
<212> TYPE: DNA
<213> ORGANISM: Artificial
<220> FEATURE:
```

<223> OTHER INFORMATION: primer

<400> SEQUENCE: 10
aaaggatccc ctaaactcct tattatattg                                            30

<210> SEQ ID NO 11
<211> LENGTH: 30
<212> TYPE: DNA
<213> ORGANISM: Artificial
<220> FEATURE:
<223> OTHER INFORMATION: primer

<400> SEQUENCE: 11
aaaggatcca aaccggagca cagactccgg                                            30

<210> SEQ ID NO 12
<211> LENGTH: 30
<212> TYPE: DNA
<213> ORGANISM: Artificial
<220> FEATURE:
<223> OTHER INFORMATION: primer

<400> SEQUENCE: 12
aaatctagaa tcagatcatc gtcgccttac                                            30

<210> SEQ ID NO 13
<211> LENGTH: 30
<212> TYPE: DNA
<213> ORGANISM: Artificial
<220> FEATURE:
<223> OTHER INFORMATION: primer

<400> SEQUENCE: 13
ttttgagctc gatcaggatt gcgttggtgg                                            30

<210> SEQ ID NO 14
<211> LENGTH: 20
<212> TYPE: DNA
<213> ORGANISM: Artificial
<220> FEATURE:
<223> OTHER INFORMATION: primer

<400> SEQUENCE: 14
cgaacagtaa tcgtacaggg                                                       20

<210> SEQ ID NO 15
<211> LENGTH: 35
<212> TYPE: DNA
<213> ORGANISM: Artificial
<220> FEATURE:
<223> OTHER INFORMATION: primer

<400> SEQUENCE: 15
tacgattact gttcggcatc gaccgaatac ccgag                                      35

<210> SEQ ID NO 16
<211> LENGTH: 30
<212> TYPE: DNA
<213> ORGANISM: Artificial
<220> FEATURE:
<223> OTHER INFORMATION: primer

<400> SEQUENCE: 16
tttttctaga cctggcacgc ctctcttctc                                            30

<210> SEQ ID NO 17

```
<211> LENGTH: 30
<212> TYPE: DNA
<213> ORGANISM: Artificial
<220> FEATURE:
<223> OTHER INFORMATION: primer

<400> SEQUENCE: 17
aacgaattct cgcaatgatt gacacgattc                              30

<210> SEQ ID NO 18
<211> LENGTH: 32
<212> TYPE: DNA
<213> ORGANISM: Artificial
<220> FEATURE:
<223> OTHER INFORMATION: primer

<400> SEQUENCE: 18
acagaattcg ctatttgtta gtgaataaaa gg                           32

<210> SEQ ID NO 19
<211> LENGTH: 28
<212> TYPE: DNA
<213> ORGANISM: Artificial
<220> FEATURE:
<223> OTHER INFORMATION: primer

<400> SEQUENCE: 19
ggaattccgg agaaagtctt atgaaact                                28

<210> SEQ ID NO 20
<211> LENGTH: 29
<212> TYPE: DNA
<213> ORGANISM: Artificial
<220> FEATURE:
<223> OTHER INFORMATION: primer

<400> SEQUENCE: 20
cccaagcttt taaaccagtt cgttcgggc                               29

<210> SEQ ID NO 21
<211> LENGTH: 26
<212> TYPE: DNA
<213> ORGANISM: Artificial
<220> FEATURE:
<223> OTHER INFORMATION: primer

<400> SEQUENCE: 21
aaggtaccac cagagcgttc tcaagc                                  26

<210> SEQ ID NO 22
<211> LENGTH: 30
<212> TYPE: DNA
<213> ORGANISM: Artificial
<220> FEATURE:
<223> OTHER INFORMATION: primer

<400> SEQUENCE: 22
gctctagatt ctccagtgat gttgaatcac                              30

<210> SEQ ID NO 23
<211> LENGTH: 28
<212> TYPE: DNA
<213> ORGANISM: Artificial
<220> FEATURE:
<223> OTHER INFORMATION: primer

<400> SEQUENCE: 23
```

```
ggtctagagc aatgattcac acgattcg                                              28
```

<210> SEQ ID NO 24
<211> LENGTH: 28
<212> TYPE: DNA
<213> ORGANISM: Artificial
<220> FEATURE:
<223> OTHER INFORMATION: primer

<400> SEQUENCE: 24

```
aactgcaggt tcgttctcat acacgtcc                                              28
```

<210> SEQ ID NO 25
<211> LENGTH: 29
<212> TYPE: DNA
<213> ORGANISM: Artificial
<220> FEATURE:
<223> OTHER INFORMATION: primer

<400> SEQUENCE: 25

```
tactgcagat ctcaataacc gctatctgg                                             29
```

<210> SEQ ID NO 26
<211> LENGTH: 28
<212> TYPE: DNA
<213> ORGANISM: Artificial
<220> FEATURE:
<223> OTHER INFORMATION: primer

<400> SEQUENCE: 26

```
gctctagata gccattgtac tggtatgg                                              28
```

<210> SEQ ID NO 27
<211> LENGTH: 27
<212> TYPE: DNA
<213> ORGANISM: Artificial
<220> FEATURE:
<223> OTHER INFORMATION: primer

<400> SEQUENCE: 27

```
tatctagatg ctcagccgta gctaagc                                               27
```

<210> SEQ ID NO 28
<211> LENGTH: 27
<212> TYPE: DNA
<213> ORGANISM: Artificial
<220> FEATURE:
<223> OTHER INFORMATION: primer

<400> SEQUENCE: 28

```
cgaattcatc catctgacat tcgctgg                                               27
```

<210> SEQ ID NO 29
<211> LENGTH: 33
<212> TYPE: DNA
<213> ORGANISM: Artificial
<220> FEATURE:
<223> OTHER INFORMATION: primer

<400> SEQUENCE: 29

```
cgagctacat atgcaatgat tgacacgatt ccg                                        33
```

<210> SEQ ID NO 30
<211> LENGTH: 29
<212> TYPE: DNA
<213> ORGANISM: Artificial
<220> FEATURE:

<223> OTHER INFORMATION: primer

<400> SEQUENCE: 30
tctagagcta tttgttagtg aataaaagg                                    29

<210> SEQ ID NO 31
<211> LENGTH: 43
<212> TYPE: DNA
<213> ORGANISM: Artificial
<220> FEATURE:
<223> OTHER INFORMATION: primer

<400> SEQUENCE: 31
gatctagacg gagaaagtct tatgacgcaa tctcgattgc atg                    43

<210> SEQ ID NO 32
<211> LENGTH: 29
<212> TYPE: DNA
<213> ORGANISM: Artificial
<220> FEATURE:
<223> OTHER INFORMATION: primer

<400> SEQUENCE: 32
atggtacctt aacccagttg ccagagtgc                                    29

<210> SEQ ID NO 33
<211> LENGTH: 40
<212> TYPE: DNA
<213> ORGANISM: Artificial
<220> FEATURE:
<223> OTHER INFORMATION: primer

<400> SEQUENCE: 33
atggtaccgg agaaagtctt atgagcagac gtgttgctac                        40

<210> SEQ ID NO 34
<211> LENGTH: 29
<212> TYPE: DNA
<213> ORGANISM: Artificial
<220> FEATURE:
<223> OTHER INFORMATION: primer

<400> SEQUENCE: 34
tcggatcctt atgcctctcc tgctgtcag                                    29

<210> SEQ ID NO 35
<211> LENGTH: 9
<212> TYPE: PRT
<213> ORGANISM: Escherichia coli

<400> SEQUENCE: 35

Met Thr Gln Ser Arg Leu His Ala Ala
1               5

<210> SEQ ID NO 36
<211> LENGTH: 43
<212> TYPE: DNA
<213> ORGANISM: Artificial
<220> FEATURE:
<223> OTHER INFORMATION: primer

<400> SEQUENCE: 36
aatctagacg gagaaagtct tatggcggaa actaccgtta agc                    43

<210> SEQ ID NO 37
<211> LENGTH: 28

```
<210> SEQ ID NO 37
<211> LENGTH: 28
<212> TYPE: DNA
<213> ORGANISM: Artificial
<220> FEATURE:
<223> OTHER INFORMATION: primer

<400> SEQUENCE: 37
ctgtctagat cagaagccga actgggcg                                28

<210> SEQ ID NO 38
<211> LENGTH: 28
<212> TYPE: DNA
<213> ORGANISM: Artificial
<220> FEATURE:
<223> OTHER INFORMATION: primer

<400> SEQUENCE: 38
gctctagagc attcctgaca gcagaagc                                28

<210> SEQ ID NO 39
<211> LENGTH: 28
<212> TYPE: DNA
<213> ORGANISM: Artificial
<220> FEATURE:
<223> OTHER INFORMATION: primer

<400> SEQUENCE: 39
aactgcagtc ggcgtgtagt agtgaacc                                28

<210> SEQ ID NO 40
<211> LENGTH: 18
<212> TYPE: DNA
<213> ORGANISM: Artificial
<220> FEATURE:
<223> OTHER INFORMATION: primer

<400> SEQUENCE: 40
caacaccaag ctttcgcg                                           18

<210> SEQ ID NO 41
<211> LENGTH: 21
<212> TYPE: DNA
<213> ORGANISM: Artificial
<220> FEATURE:
<223> OTHER INFORMATION: primer

<400> SEQUENCE: 41
tgttctagaa agttctttga c                                       21

<210> SEQ ID NO 42
<211> LENGTH: 28
<212> TYPE: DNA
<213> ORGANISM: Artificial
<220> FEATURE:
<223> OTHER INFORMATION: primer

<400> SEQUENCE: 42
ggaagcttca aattggcgtc tctgatct                                28

<210> SEQ ID NO 43
<211> LENGTH: 35
<212> TYPE: DNA
<213> ORGANISM: Artificial
<220> FEATURE:
<223> OTHER INFORMATION: primer

<400> SEQUENCE: 43
aaacccgggc catccatata gtggaacagg aacgg                        35
```

<210> SEQ ID NO 44
<211> LENGTH: 28
<212> TYPE: DNA
<213> ORGANISM: Artificial
<220> FEATURE:
<223> OTHER INFORMATION: primer

<400> SEQUENCE: 44
gggctcgagt ggcgatgacg ctgactgg                                         28

<210> SEQ ID NO 45
<211> LENGTH: 38
<212> TYPE: DNA
<213> ORGANISM: Artificial
<220> FEATURE:
<223> OTHER INFORMATION: primer

<400> SEQUENCE: 45
cgtctagaac gggtaaatct ggtggtgacc gtcacccg                              38

<210> SEQ ID NO 46
<211> LENGTH: 43
<212> TYPE: DNA
<213> ORGANISM: Artificial
<220> FEATURE:
<223> OTHER INFORMATION: primer

<400> SEQUENCE: 46
aagaattccg gagaaagtct tatggcggaa actaccgtta agc                        43

<210> SEQ ID NO 47
<211> LENGTH: 28
<212> TYPE: DNA
<213> ORGANISM: Artificial
<220> FEATURE:
<223> OTHER INFORMATION: primer

<400> SEQUENCE: 47
ctgtctagat cagaagccga actgggcg                                         28

<210> SEQ ID NO 48
<211> LENGTH: 29
<212> TYPE: DNA
<213> ORGANISM: Artificial
<220> FEATURE:
<223> OTHER INFORMATION: primer

<400> SEQUENCE: 48
ggtctagagc aatgattgac acgattccg                                        29

<210> SEQ ID NO 49
<211> LENGTH: 31
<212> TYPE: DNA
<213> ORGANISM: Artificial
<220> FEATURE:
<223> OTHER INFORMATION: primer

<400> SEQUENCE: 49
cggaattccg ctatttgtta gtgaataaaa g                                     31

<210> SEQ ID NO 50
<211> LENGTH: 56
<212> TYPE: DNA
<213> ORGANISM: Artificial
<220> FEATURE:
<223> OTHER INFORMATION: primer

```
<400> SEQUENCE: 50
ccaagcttct gcaggtcgac ggatccgagc tcagctattt gttagtgaat aaaagg        56

<210> SEQ ID NO 51
<211> LENGTH: 40
<212> TYPE: DNA
<213> ORGANISM: Artificial
<220> FEATURE:
<223> OTHER INFORMATION: primer

<400> SEQUENCE: 51
gcggatccgc tggtggaata tatgacgcaa tctcgattgc                          40

<210> SEQ ID NO 52
<211> LENGTH: 32
<212> TYPE: DNA
<213> ORGANISM: Artificial
<220> FEATURE:
<223> OTHER INFORMATION: primer

<400> SEQUENCE: 52
gacgcgtcga cttaacccag ttgccagagt gc                                  32

<210> SEQ ID NO 53
<211> LENGTH: 44
<212> TYPE: DNA
<213> ORGANISM: Artificial
<220> FEATURE:
<223> OTHER INFORMATION: primer

<400> SEQUENCE: 53
cctgtcgacg ctggtggaat atatgagttc tgaaagtagt cagg                     44

<210> SEQ ID NO 54
<211> LENGTH: 29
<212> TYPE: DNA
<213> ORGANISM: Artificial
<220> FEATURE:
<223> OTHER INFORMATION: primer

<400> SEQUENCE: 54
ctactgcagc tacttctggg agcgccaca                                      29
```